US012102746B2

United States Patent
Ito et al.

(10) Patent No.: US 12,102,746 B2
(45) Date of Patent: Oct. 1, 2024

(54) CONNECTION STRUCTURE AND BLOOD PURIFYING DEVICE

(71) Applicant: Nikkiso Company Limited, Tokyo (JP)

(72) Inventors: Hikaru Ito, Shizouka (JP); Fumitoshi Henmi, Shizouka (JP); Takayuki Suzuki, Shizouka (JP); Masahiro Toyoda, Shizouka (JP)

(73) Assignee: Nikkiso Company Limited, Tokyo (JP)

( * ) Notice: Subject to any disclaimer, the term of this patent is extended or adjusted under 35 U.S.C. 154(b) by 657 days.

(21) Appl. No.: 17/311,058

(22) PCT Filed: Dec. 2, 2019

(86) PCT No.: PCT/JP2019/047010
§ 371 (c)(1),
(2) Date: Jun. 4, 2021

(87) PCT Pub. No.: WO2020/116385
PCT Pub. Date: Jun. 11, 2020

(65) Prior Publication Data
US 2022/0016327 A1   Jan. 20, 2022

(30) Foreign Application Priority Data
Dec. 6, 2018  (JP) ................................. 2018-228862

(51) Int. Cl.
*A61M 1/36* (2006.01)
*A61M 1/34* (2006.01)
(Continued)

(52) U.S. Cl.
CPC .......... *A61M 1/367* (2013.01); *A61M 1/3609* (2014.02); *A61M 39/10* (2013.01);
(Continued)

(58) Field of Classification Search
CPC .............. A61M 1/3641; A61M 1/3639; A61M 1/3621; A61M 1/14; A61M 1/3413;
(Continued)

(56) References Cited

U.S. PATENT DOCUMENTS 4,798,090 A  *  1/1989  Heath ............... A61M 1/36226
                                                    210/90
8,642,088 B2    2/2014  Reed et al.
(Continued)

FOREIGN PATENT DOCUMENTS

CN          104363936 A      2/2015
CN          107614032 A      1/2018
(Continued)

OTHER PUBLICATIONS

International Search Report for Application No. PCT/JP2019/047010, dated Feb. 10, 2020.
(Continued)

*Primary Examiner* — Nicholas J. Weiss
*Assistant Examiner* — Linnae E. Raymond
(74) *Attorney, Agent, or Firm* — Young Basile Hanlon & MacFarlane, P.C.

(57) ABSTRACT

A connection structure includes a chamber comprising a hollow housing, a diaphragm dividing the inside of the housing into a first space and a second space, and an output port outputting a gas in the second space with deformation of the diaphragm caused by pressure of a fluid flowing into the first space; a connection part comprising a coupling connected to the output port and being attached to a pressure detection device comprising a pressure sensor for detecting pressure of the gas output from the coupling; and a seal member being sandwiched between a side surface of the output port and a side surface of the coupling and moving
(Continued)

while changing a sealing position when connecting or extracting the chamber to/from the connection part.

9 Claims, 19 Drawing Sheets

(51) Int. Cl.
*A61M 39/10* (2006.01)
*A61M 39/20* (2006.01)
(52) U.S. Cl.
CPC ........... *A61M 39/20* (2013.01); *A61M 1/3413* (2013.01); *A61M 2039/1072* (2013.01); *A61M 2205/3331* (2013.01)
(58) Field of Classification Search
CPC .. A61M 2039/1072; A61M 1/34; A61M 1/36; A61M 2039/1027; A61M 2039/1083; A61M 2039/1088
See application file for complete search history.

(56) References Cited

U.S. PATENT DOCUMENTS

| | | | |
|---|---|---|---|
| 8,960,010 | B1 | 2/2015 | Crnkovich et al. |
| 9,545,423 | B2 | 1/2017 | Reed et al. |
| 9,833,554 | B2 | 12/2017 | Crnkovich et al. |
| 10,104,888 | B2 | 10/2018 | Reed et al. |
| 10,441,704 | B2 | 10/2019 | Crnkovich et al. |
| 10,912,876 | B2 | 2/2021 | Crnkovich et al. |
| 2011/0059162 | A1 | 3/2011 | Reed et al. |
| 2014/0134238 | A1 | 5/2014 | Reed et al. |
| 2015/0306299 | A1* | 10/2015 | Stuva ...................... A61M 1/16 604/121 |
| 2016/0228631 | A1 | 8/2016 | Crnkovich et al. |
| 2017/0142967 | A1 | 5/2017 | Reed et al. |
| 2017/0290972 | A1* | 10/2017 | Case ................... A61M 1/3639 |
| 2018/0080843 | A1 | 3/2018 | Funamura et al. |
| 2018/0093033 | A1 | 4/2018 | Crnkovich et al. |
| 2018/0318491 | A1 | 11/2018 | Schnell et al. |
| 2019/0336673 | A1 | 11/2019 | Crnkovich et al. |

FOREIGN PATENT DOCUMENTS

| | | | |
|---|---|---|---|
| EP | 3305344 A1 | 4/2018 | |
| JP | S6196281 A * | 5/1986 | |
| JP | 2000257781 A * | 9/2000 | ............ F16L 19/061 |
| JP | 2006220455 A | 8/2006 | |
| JP | 2007198393 A | 8/2007 | |
| JP | 201156011 A | 3/2011 | |
| JP | 2015027444 A * | 2/2015 | |
| JP | 2017504389 A | 2/2017 | |
| JP | 201780078 A | 5/2017 | |
| JP | 2018146318 A | 9/2018 | |
| WO | WO-2016194944 A1 * | 12/2016 | ............. A61B 5/021 |

OTHER PUBLICATIONS

European Search Report for Application No. 19892978.8, dated Jun. 23, 2022, 7 pgs.

Chinese Office Action for Application No. 201980080204.1, dated Nov. 28, 2023, with English translation, 19 pgs.

\* cited by examiner

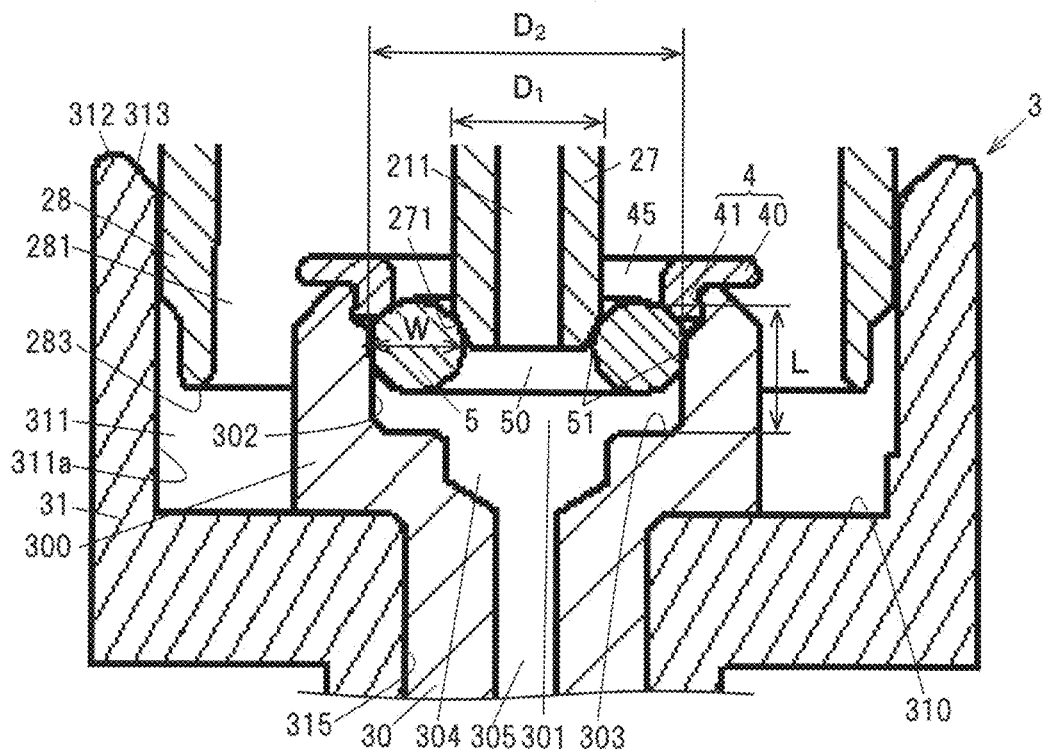
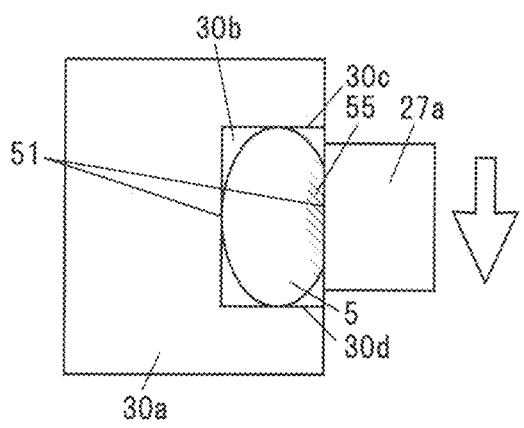 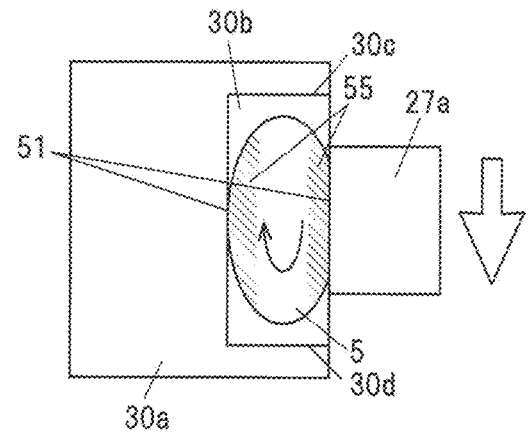

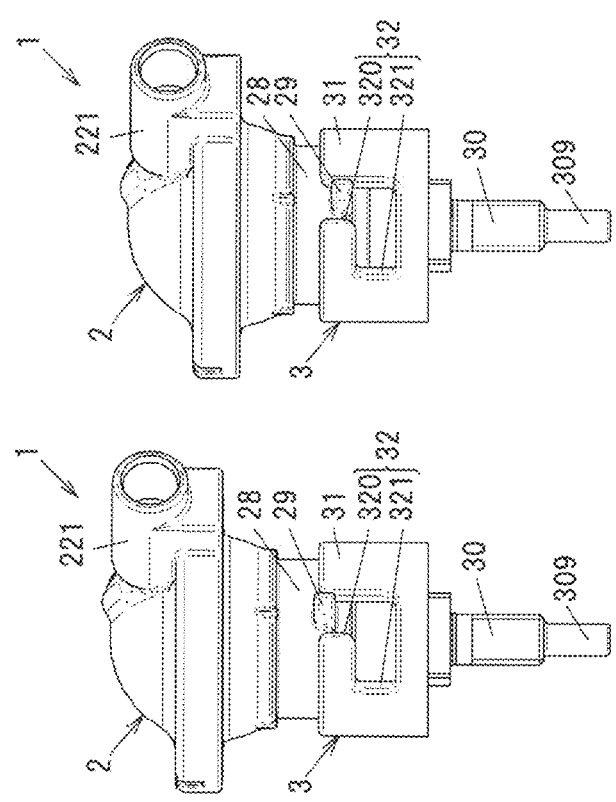

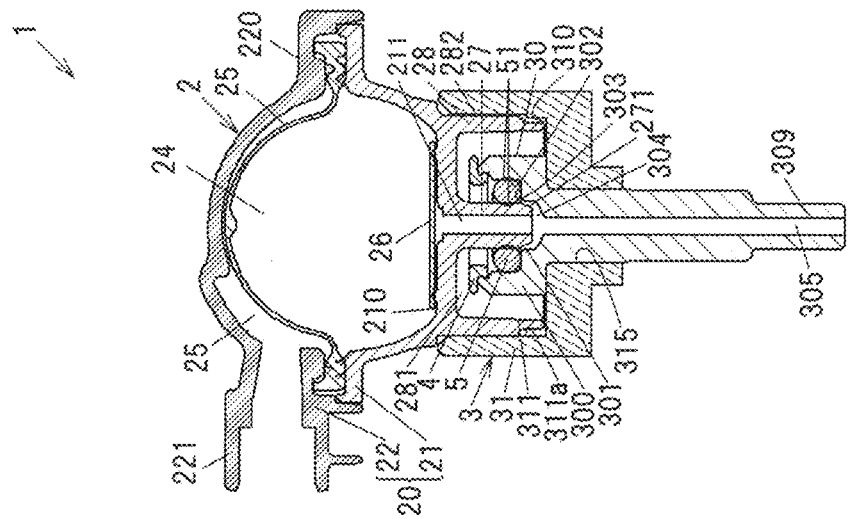
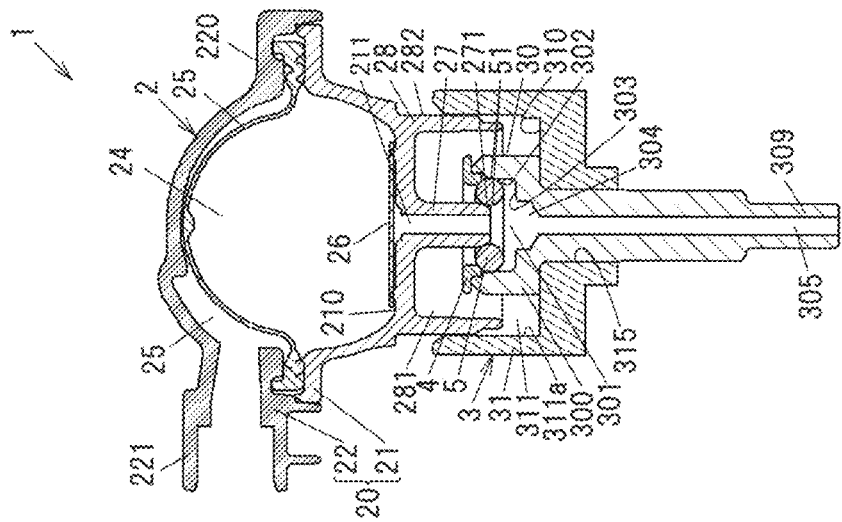
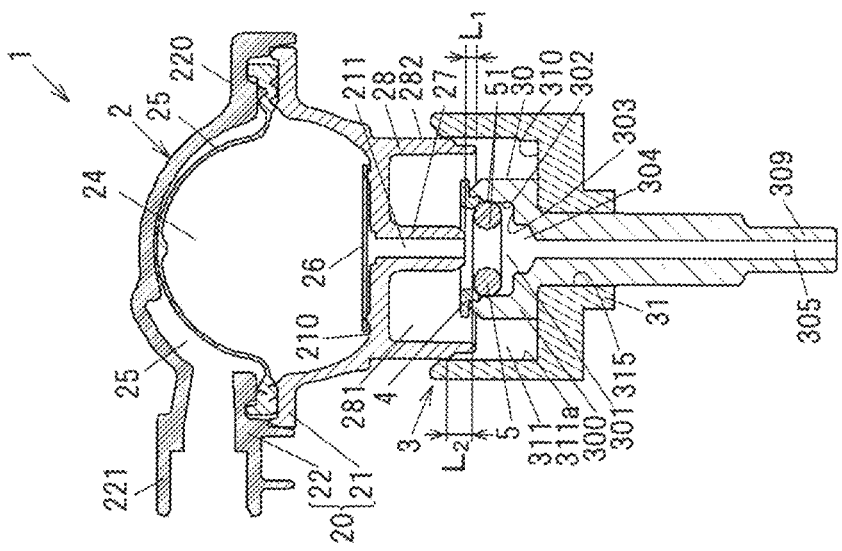

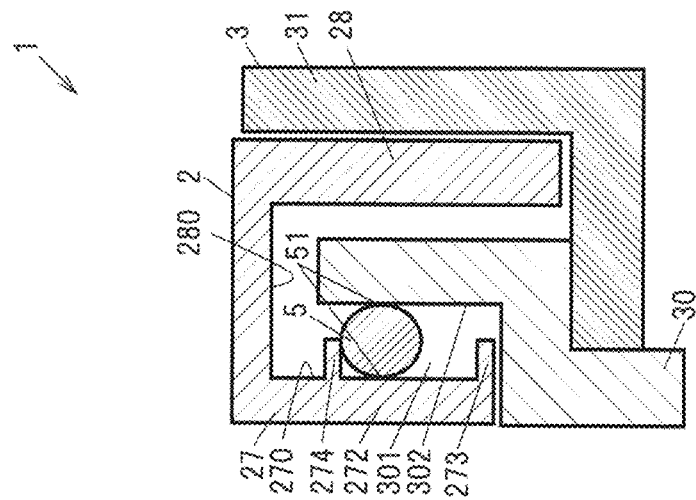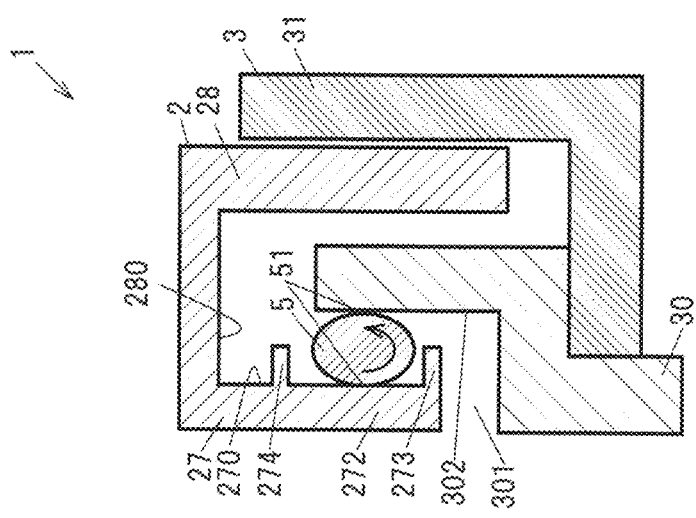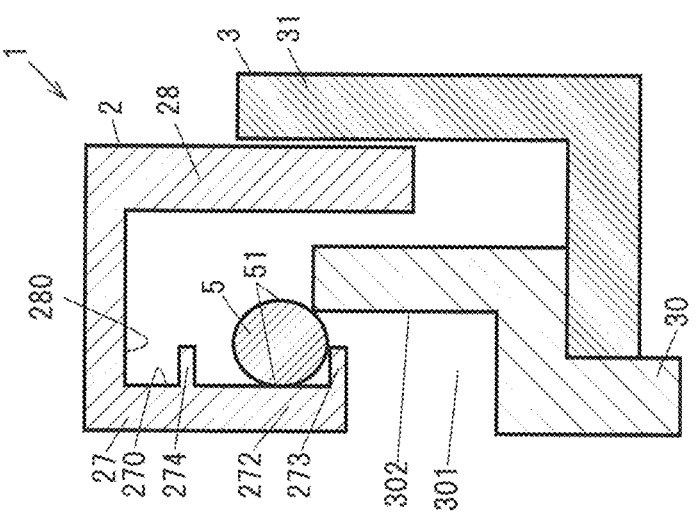

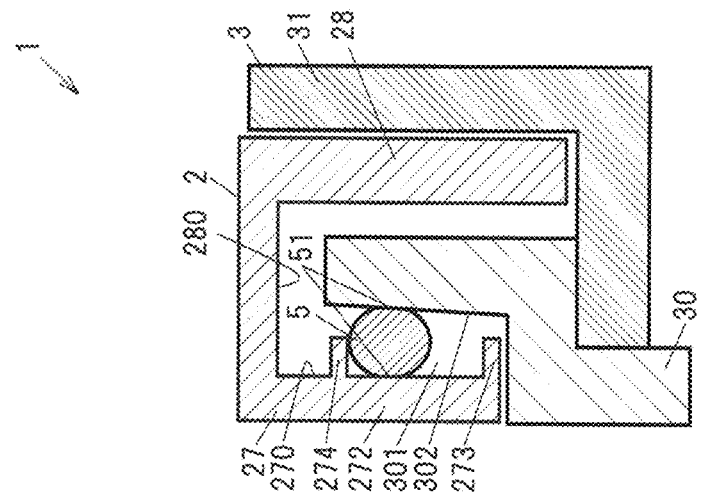
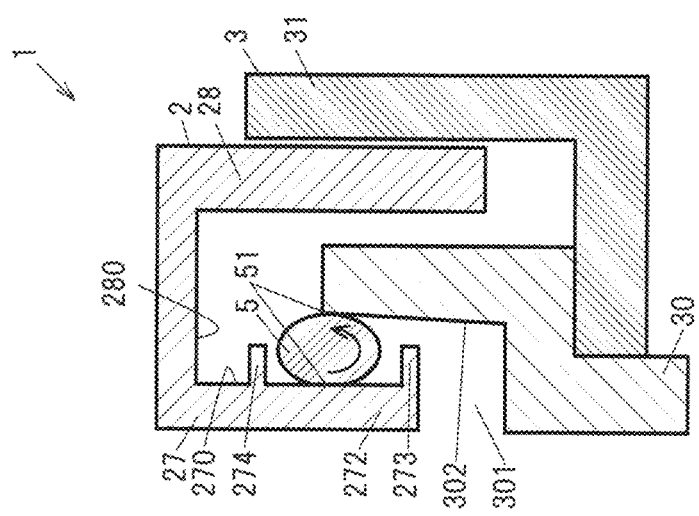
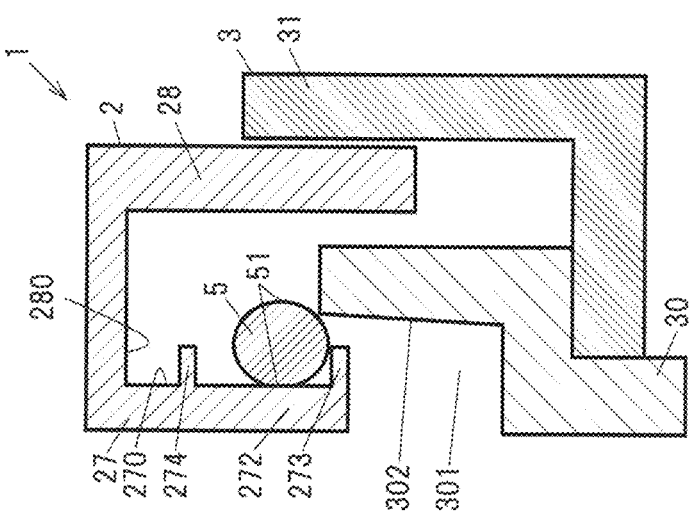

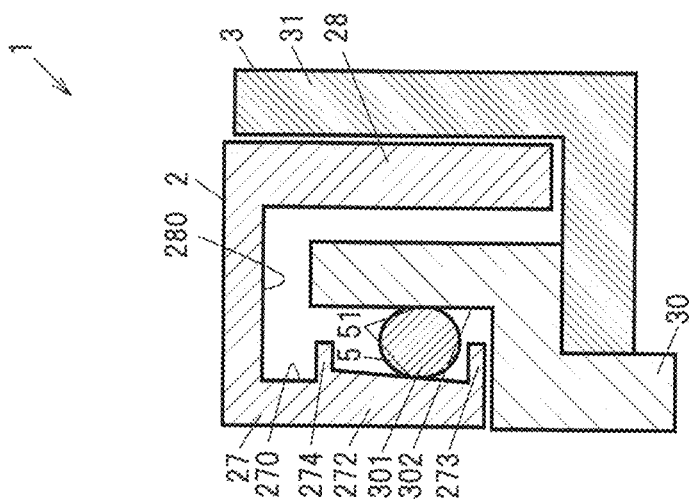
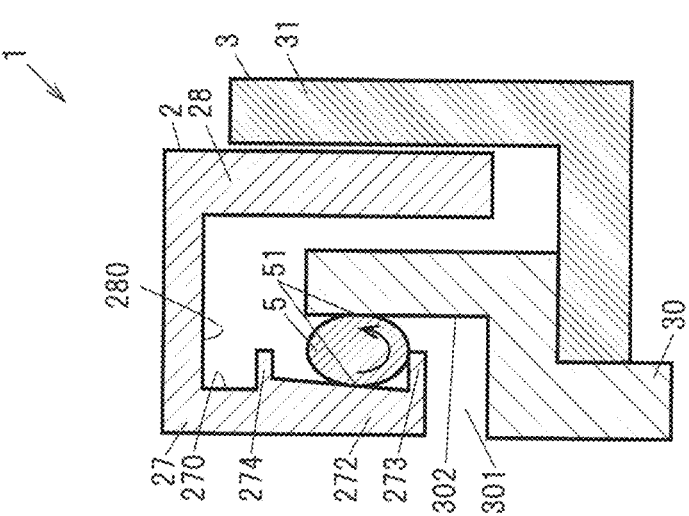
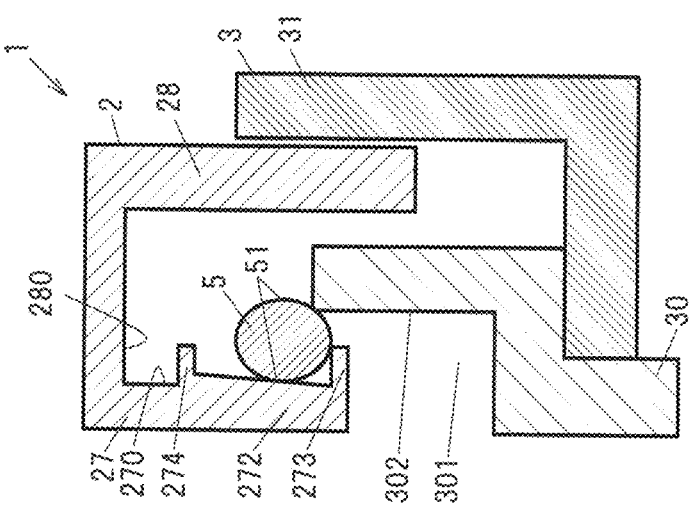

CONNECTION STRUCTURE AND BLOOD PURIFYING DEVICE

CROSS-REFERENCE TO RELATED APPLICATION(S)

This application is a continuation of International Application No. PCT/JP2019/0047010, filed on Dec. 2, 2019, which claims priority to Japanese Application No. 2018-228862, filed on Dec. 6, 2018, the entire disclosures of which are hereby incorporated by reference.

TECHNICAL FIELD

The invention relates to a connection structure and a blood purifying device.

BACKGROUND ART

Pressure pods are known as a conventional technique, which are used for detecting pressure of blood in a blood circuit extracorporeally circulating blood taken from a patient and returning to the body during dialysis treatment (blood purification treatment) (see, e.g., Patent Document 1).

The inside of the pressure pod is divided into a flow-through fluid side and a gas side by a diaphragm, and a pressure sensor is connected on the gas side. The pressure sensor detects pressure resulting from movement of the diaphragm caused by pressure of blood that is a flow-through fluid. The pressure of the blood in the blood circuit can be detected based on the pressure detected by the pressure sensor.

CITATION LIST

Patent Literature

Patent Document 1: Japanese Translation of PCT International Application Publication No. JP-T 2017-504389

SUMMARY OF INVENTION

Technical Problem

Such conventional pressure pods are discarded after a single use since the blood circulates thereinside. Thus, when, e.g., the conventional pressure pod is connected to the pressure sensor with a seal member interposed therebetween, the seal member is rubbed each time connecting or extracting the pressure pod and the surface thereof becomes rough, which may cause a decrease in durability.

Therefore, it is an object of the invention to provide a connection structure and a blood purifying device that are capable of enhancing durability of a seal member.

Solution To Problem

According to one aspect of the invention, a connection structure of variation 1 may comprise a chamber comprising a hollow housing, a diaphragm dividing the inside of the housing into a first space and a second space, and an output port outputting a gas in the second space with deformation of the diaphragm caused by pressure of a fluid flowing into the first space; a connection part comprising a coupling connected to the output port and being attached to a pressure detection device comprising a pressure sensor for detecting pressure of the gas output from the coupling; and a seal member being sandwiched between a side surface of the output port and a side surface of the coupling and moving while changing a sealing position when connecting or extracting the chamber to/from the connection part.

Variation 2 is the connection structure according to variation 1, wherein at least one of the side surface of the output port and the side surface of the coupling has a tapered shape.

The variation 3 is the connection structure according to variation 1 or 2, comprising: a first stopper being arranged on the side surface of the output port or on the side surface of the coupling and defining a position of the seal member to prevent the seal member from coming off; and a second stopper being arranged on the side surface of the output port or on the side surface of the coupling at a position facing the first stopper and separated from the first stopper by more than a diameter of the seal member.

Variation 4 is the connection structure according to variation 3, wherein the coupling comprises, at an end facing the chamber, an insertion opening allowing insertion of the seal member and being connected to a flow route of the gas, the first stopper is provided on an end side of the insertion opening, and a bottom surface of the insertion opening serves as the second stopper.

Variation 5 is the connection structure according to variation 4, wherein the first stopper comprises a cap attached to the end.

Variation 6 is the connection structure according to any one of variations 1 to 5, wherein the chamber comprises a cylindrical insertion part comprising a first bottom surface and is configured that the output port is provided so as to protrude from the first bottom surface, the connection part comprises a cylindrical guide part comprising a second bottom surface and is configured that the coupling is provided so as to protrude from the second bottom surface, and the chamber and the connection part are connected by inserting the insertion part into an opening of the guide part.

A blood purifying device of variation 7 may comprise: the connection structure according to any one of variations 1 to 6; a liquid circuit capable of circulating human blood or dialysate; and a blood purifying device-main body to which the liquid circuit is attached via the connection structure and which purifies the blood while detecting, as the pressure detection device, pressure of the blood or dialysate circulating in the liquid circuit.

Variation 8 is the blood purifying device according to variation 7, wherein the liquid circuit is a disposable product to be discarded after each blood purification treatment, the chamber is provided on the liquid circuit, and the connection part and the seal member are provided in the blood purifying device-main body.

Variation 9 is a blood purifying device, comprising: the connection structure according to any one of variations 1 to 6; a liquid circuit being capable of circulating human blood or dialysate and being a disposable product to be discarded after each blood purification treatment; a blood purifying device-main body to which the liquid circuit is attached via the connection structure; and a sealing member removably sealing the seal member inside the blood purifying device-main body, wherein the chamber is provided on the liquid circuit, and the connection part and the seal member are provided in the blood purifying device-main body.

Advantageous Effects of Invention

According to the invention described in claims 1 to 7, it is possible to enhance durability of the seal member.

According to the invention described in claim 2, providing the tapered shape allows the seal member to move while changing the sealing position.

According to the invention described in claims 3 and 4, providing the first stopper and the second stopper at a distance allows the seal member to move while changing the sealing position.

According to the invention described in claim 5, it is easy to replace the seal member.

According to the invention described in claim 6, the output port can be stably connected to coupling by a guiding action of the insertion part and the guide part.

According to the invention described in claims 8 and 9, since the seal member is arranged on the durable blood purifying device-main body, not on the disposable liquid circuit, it is not necessary to discard the seal member after each treatment and it is thus possible to reduce the cost for the liquid circuit.

BRIEF DESCRIPTION OF DRAWINGS

FIG. 5A is a diagram for explaining an example of a squashing rate of the O-ring in the first embodiment.

FIG. 5B is an explanatory diagram illustrating an example of a region damaged when the O-ring in the first embodiment does not rotate.

FIG. 5C is an explanatory diagram illustrating an example of a region damaged when the O-ring in the first embodiment rotates.

FIG. 6A is a diagram illustrating an example of alignment between the chamber and the connection part in the connection structure of the first embodiment.

FIG. 6B is a diagram illustrating an example of when the chamber is pushed into the connection part in the connection structure of the first embodiment.

FIG. 6C is a diagram illustrating an example of when the chamber is further pushed into the connection part in the connection structure of the first embodiment.

FIG. 6D is a diagram illustrating an example of when the chamber is rotated and locked in the connection structure of the first embodiment.

FIG. 7A is a cross sectional view showing the example of alignment between the chamber and the connection part in the connection structure of the first embodiment.

FIG. 7B is a cross sectional view showing the example of when the chamber is pushed into the connection part in the connection structure of the first embodiment.

FIG. 7C is a cross sectional view showing the example of when the chamber is further pushed into the connection part in the connection structure of the first embodiment.

FIG. 10A is a diagram illustrating an example at the start of insertion of the chamber into the connection part in the connection structure of the fourth embodiment.

FIG. 10B is a diagram illustrating an example during insertion of the chamber into the connection part in the connection structure of the fourth embodiment.

FIG. 10C is a diagram illustrating an example at the end of insertion of the chamber into the connection part in the connection structure of the fourth embodiment.

FIG. 11A is a diagram illustrating an example at the start of insertion of the chamber into the connection part in the connection structure of the fifth embodiment.

FIG. 11B is a diagram illustrating an example during insertion of the chamber into the connection part in the connection structure of the fifth embodiment.

FIG. 11C is a diagram illustrating an example at the end of insertion of the chamber into the connection part in the connection structure of the fifth embodiment.

FIG. 12A is a diagram illustrating an example at the start of insertion of the chamber into the connection part in the connection structure of the sixth embodiment.

FIG. 12B is a diagram illustrating an example during insertion of the chamber into the connection part in the connection structure of the sixth embodiment.

FIG. 12C is a diagram illustrating an example at the end of insertion of the chamber into the connection part in the connection structure of the sixth embodiment.

DESCRIPTION OF EMBODIMENTS

First Embodiment

General Configuration of Blood Purifying Device 9

Figure 1A:
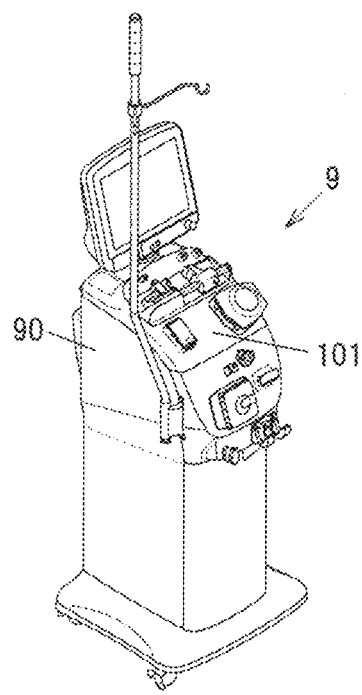
FIG. 1A is a diagram illustrating an example of a blood purifying device using a connection structure in the first embodiment.
Figure 1B:
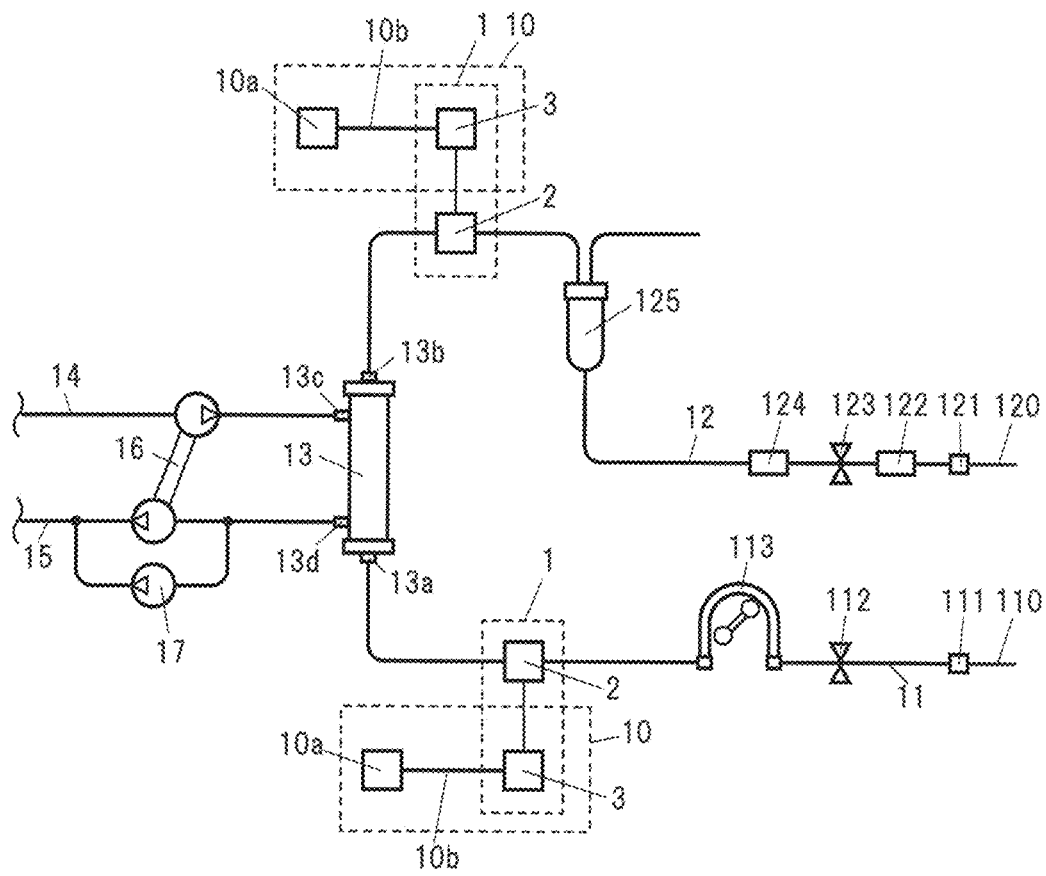
FIG. 1B is a diagram illustrating an example configuration of the blood purifying device in the first embodiment.
Figure 2A:
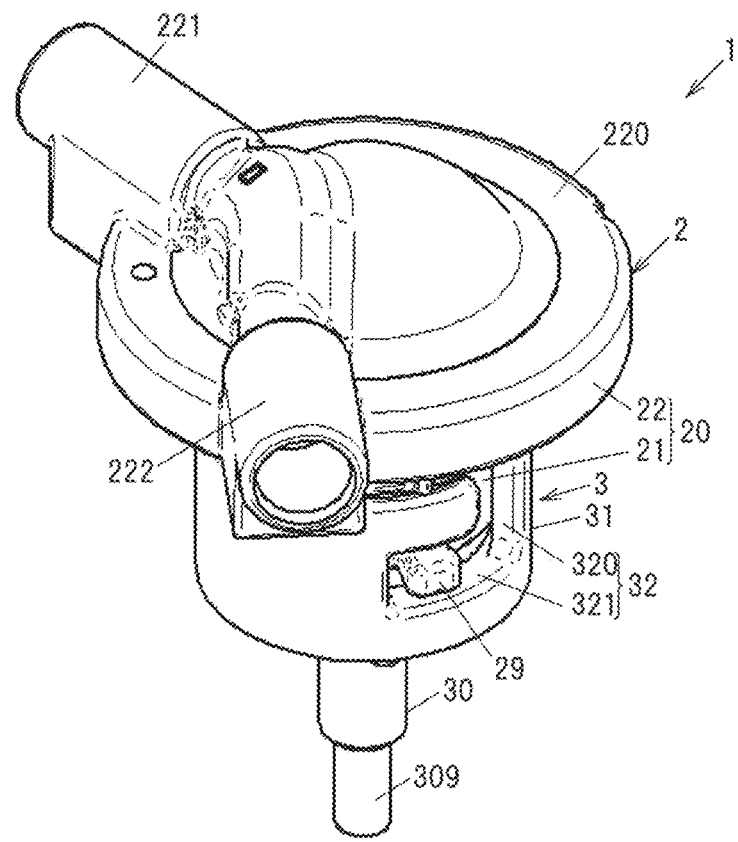
FIG. 2A is a perspective view showing an example of the connection structure in the first embodiment.
Figure 2B:
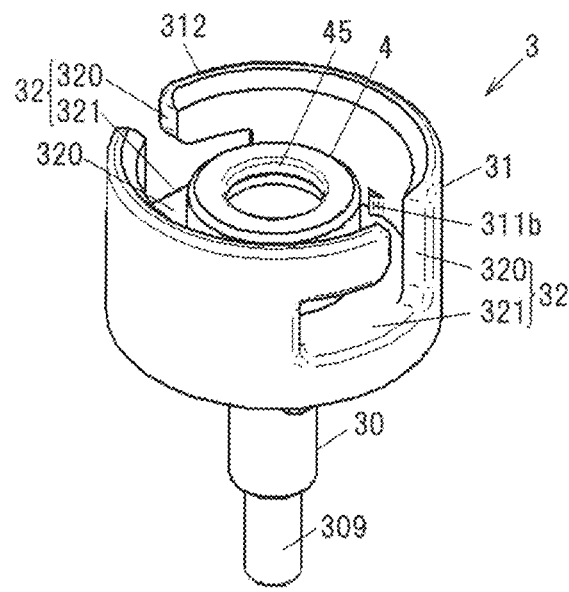
FIG. 2B is a diagram illustrating an example of a connection part constituting the connection structure in the first embodiment.
Figure 3A:
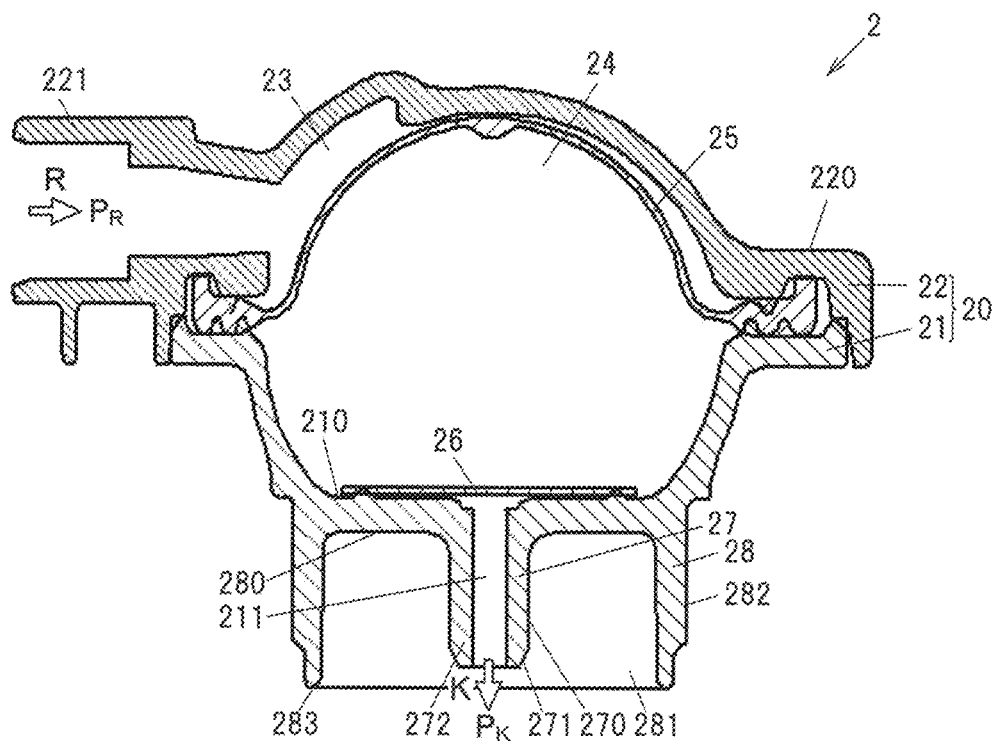
FIG. 3A is a cross sectional view showing an example of a chamber in the first embodiment.
Figure 3B:
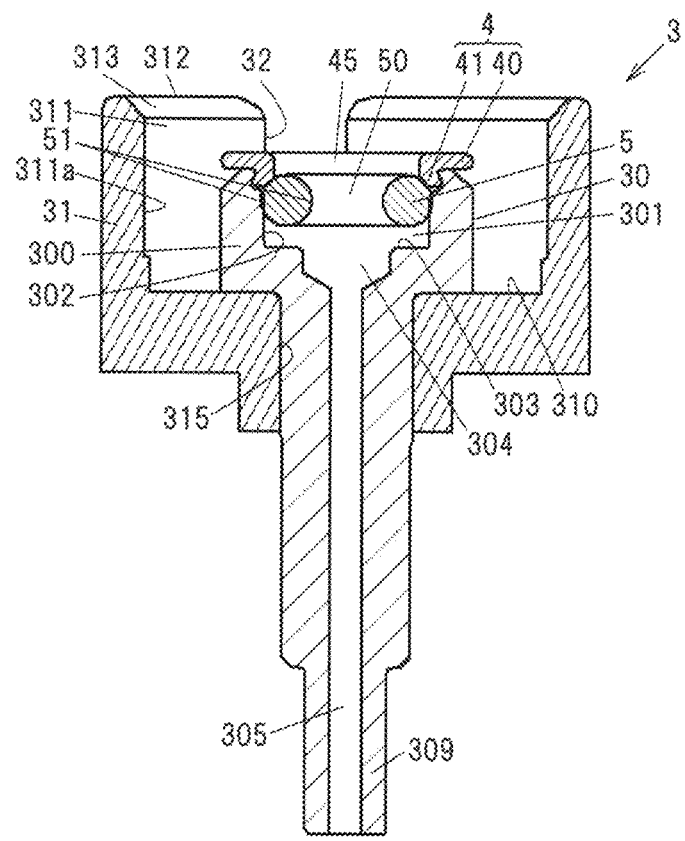
FIG. 3B is a cross sectional view showing an example of the connection part and an O-ring in the first embodiment.
Figure 4A:
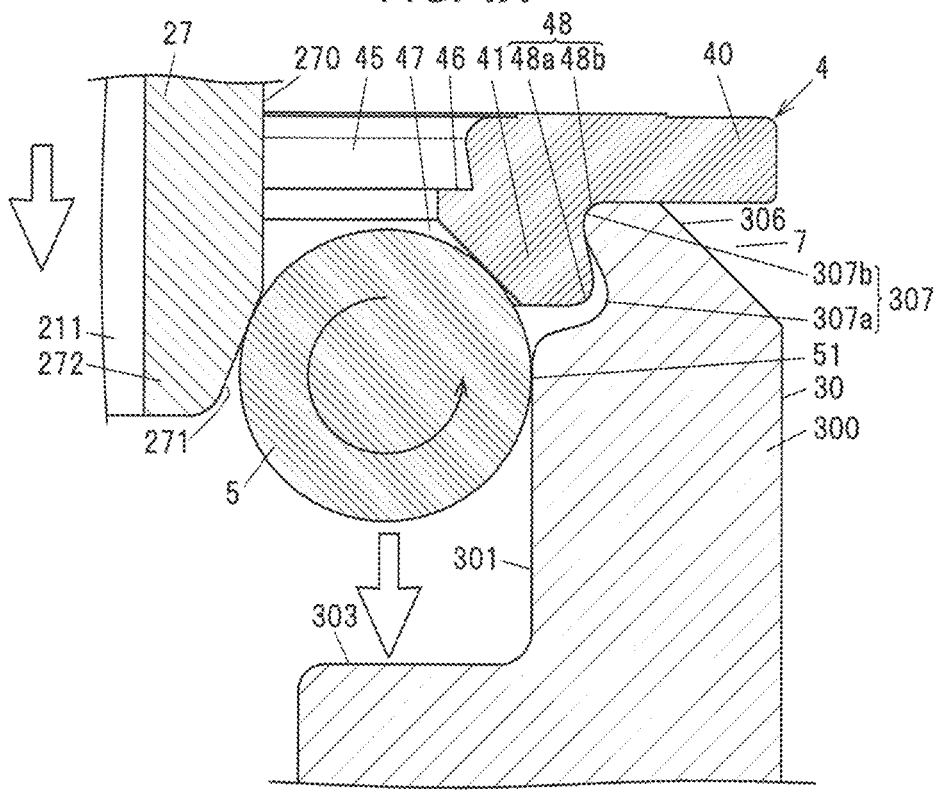
FIG. 4A is an explanatory cross-sectional view showing an example of a position of the O-ring when inserting the chamber of the connection structure in the first embodiment.
Figure 4B:
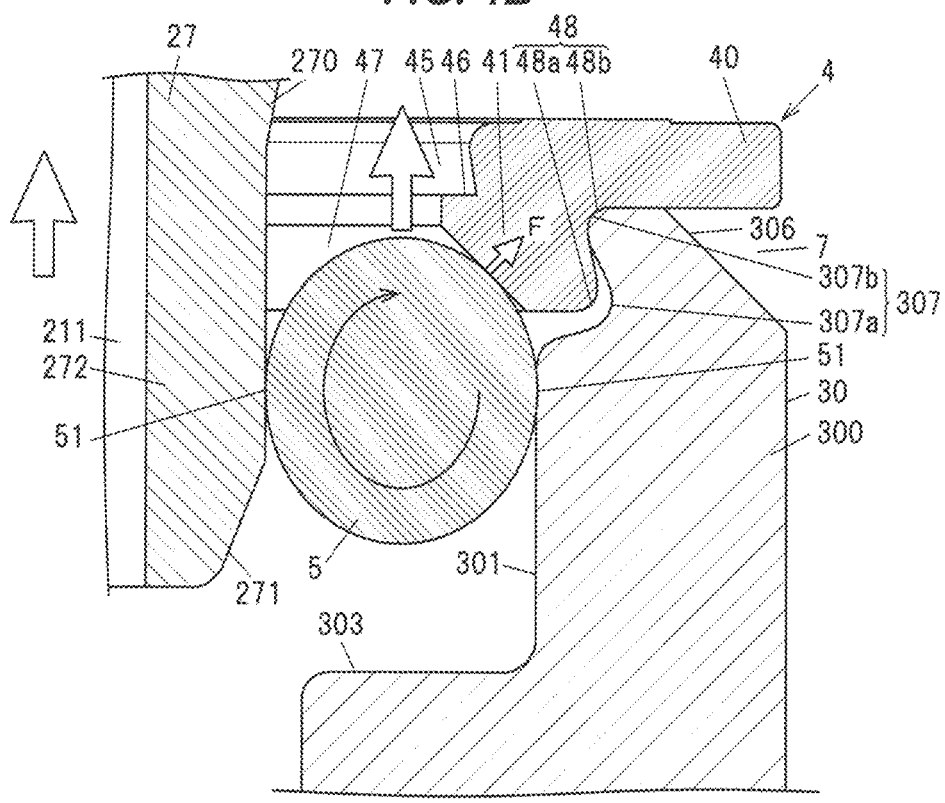
FIG. 4B is an explanatory cross-sectional view showing an example of the position of the O-ring when extracting the chamber in the first embodiment.

FIG. 1A is a diagram illustrating an example of a blood purifying device using a connection structure in the first embodiment, and FIG. 1B is a diagram illustrating an example configuration of the blood purifying device. FIG. 2A is a perspective view showing an example of the connection structure in the first embodiment, and FIG. 2B is a diagram illustrating an example of a connection part constituting the connection structure. FIG. 3A is a cross sectional view showing an example of a cross section of a chamber in the first embodiment, and FIG. 3B is a cross sectional view showing an example of the connection part and an O-ring. FIG. 4A is an explanatory cross-sectional view showing an example of a position of the O-ring when inserting the chamber of the connection structure in the first embodiment, and FIG. 4B is an explanatory cross-sectional view showing an example of the position of the O-ring when extracting the chamber. In each drawing of the embodiments described below, a scale ratio may be different from an actual ratio. The numerical range described as "A-B" means "not less than A and not more than B".

A blood purifying device 9 shown in FIG. 1A is to perform dialysis treatment (blood purification treatment). The blood purifying device 9 is provided with, e.g., connection structures 1, pressure detection units 10, an artery-side blood circuit 11, a vein-side blood circuit 12, a dialyzer 13, a dialysate introduction line 14, a dialysate discharge line 15, and a duplex pump 16, as shown in FIGS. 1A and 1B. Of those, the pressure detection units 10, the dialysate introduction line 14, the dialysate discharge line 15 and the duplex pump 16 are configured as a main body 90. The artery-side blood circuit 11, the vein-side blood circuit 12 and the dialyzer 13 are removably attached to the main body 90. At least one of the artery-side blood circuit 11 and the vein-side blood circuit 12 can be expressed as a blood circuit, at least one of the dialysate introduction line 14 and the dialysate discharge line 15 can be expressed as a dialysate circuit, and each of the blood circuit and the dialysate circuit can he expressed as a liquid circuit.

The artery-side blood circuit 11 generally includes an artery-side puncture needle 110 puncturing an artery of a patient, a connector 111 to which the artery-side puncture needle 110 is connected, a clamp 112 controlling a blood flow by opening/closing a valve, a blood pump 113 which is a peristaltic pump, and the pressure detection unit 10 connected to the artery-side blood circuit 11 via the connection structure 1, The artery-side blood circuit 11 is connected to a blood introduction port 13a of the dialyzer 13.

The vein-side blood circuit 12 generally includes a vein-side puncture needle 120 puncturing a vein of the patient, a. connector 121 to which the vein-side puncture needle 120 is connected, a blood determination unit 122 for determining whether the fluid flowing through the blood circuit is blood, a clamp 123 controlling the blood flow by opening closing a valve, an air bubble detection unit 124 for detecting air bubbles mixed in the fluid flowing through the blood circuit, a vein chamber 125 for separating air bubbles mixed in the fluid, and the pressure detection unit 10 connected to the vein-side blood circuit 12 via the connection structure 1. The vein-side blood circuit 12 is connected to a blood discharge port 13b of the dialyzer 13.

When the blood pump 113 is activated while puncturing with the artery-side puncture needle 110 and the vein-side puncture needle 120, blood of a patient reaches the dialyzer 13 through the artery-side blood circuit 11, is then subjected to blood purification treatment by the dialyzer 13, and return into the patient's body through the vein-side blood circuit 12.

The dialyzer 13 includes the blood introduction port 13a, the blood discharge port 13b, a dialysate introduction port 13c, and a dialysate discharge port 13d, The dialysate introduction port 13c and the dialysate discharge port 13d are respectively connected to the dialysate introduction line 14 and the dialysate discharge line 15 that extend from the main body 90 of the blood purifying device 9.

The dialyzer 13 has plural hollow fibers and is configured to purify blood by the hollow fibers. A blood flow route connecting the blood introduction port 13a and the blood discharge port 13b via a blood purification membrane and a dialysate flow route connecting the dialysate introduction port 13c and the dialysate discharge 13d are also formed in the dialyzer 13. The hollow fibers constituting the blood purification membrane form a hollow fiber membrane with microscopic holes penetrating an outer peripheral surface and an inner peripheral surface, and impurities, etc., in the blood are transferred into the dialysate through the hollow fiber membrane.

The duplex pump 16 is arranged in the main body 90 of the blood purifying device 9 over the dialysate introduction line 14 and the dialysate discharge line 15. Then, a water removal pump 17 is connected to the dialysate discharge line 15 so as to bypass the duplex pump 16. The water removal pump 17 is provided to remove water from the patient's blood flowing through the dialyzer 13.

One end of the dialysate introduction line 14 is connected to the dialyzer 13 and the other end is connected to a concentration adjustment means for adjusting a dialysate to a predetermined concentration, The concentration adjustment means is arranged in the blood purifying device 9 or in a dialysate supply device that supplies a dialysate to the blood purifying device 9, Meanwhile, one end of the dialysate discharge line 15 is connected to the dialyzer 13 and the other end is connected to a liquid discharge means. The dialysate reaches the dialyzer 13 from the dialysate supply device through the dialysate introduction line 14 and is then sent to the liquid discharge means through the dialysate discharge line 15.

The pressure detection units 10 are connected to the artery-side blood circuit 11 and the vein-side blood circuit 12. The pressure detection units 10 are configured to detect pressure $P_R$ of the blood flowing through the artery-side blood circuit 11 and the vein-side blood circuit 12. The pressure detection unit 10 is configured such that a pressure sensor 10a arranged in a panel 101 of the main body 90 of the blood purifying device 9 is connected to a connection part 3 of the connection structure 1 by a tube 10b.

In particular, as shown in FIGS. 2A to 3B, the connection structure 1 generally includes a chamber 2 which has a hollow housing 20, a diaphragm 25 dividing the inside of the housing 20 into a first space 23 and a second space 24, and an output port 27 outputting a gas K in the second space 24 with deformation of the diaphragm 25 caused by the pressure $P_R$ of a fluid (blood R) flowing into the first space 23, the connection part 3 which has a coupling 30 connected to the output port 27 and is attached to the main body 90 as the pressure detection device having the pressure sensor 10a for detecting pressure $P_R$ of the gas K output from the coupling 30, and a seal member that is sandwiched between a side surface 270 of the output port 27 and a side surface 302 of the coupling 30 and moves while changing a sealing position when connecting or extracting the chamber 2 to/from the connection part 3. The fluid is blood in the first embodiment but is not limited thereto, and may be another fluid such as a dialysate. The pressure detection unit 10 is also configured to indirectly detect the pressure $P_R$ of the blood R by detecting the pressure $P_K$ of the gas K resulting from deformation of the diaphragm 25 caused by the pressure $P_R$ of the blood R. The seal member is an O-ring 5 having a ring shape in the first embodiment but it is not limited thereto as long as it can move while changing the sealing position at the time of connection and extraction, i.e., at the time of insertion and extraction. The O-ring 5 moves along an insertion/extraction direction of the chamber 2 while changing the sealing position. In particular, when the chamber 2 is inserted, the O-ring 5 rotates so that its inner side moves in the insertion direction, i.e., rotates counterclockwise on the paper of FIG. 4A. When the chamber 2 is extracted, the O-ring 5 rotates so that its inner side moves in the extraction direction, i.e., rotates clockwise on the paper of FIG. 4A. Regarding the insertion/extraction direction, the insertion direction is a direction from top to bottom (a direction of an arrow shown on the left side) on the paper of FIG. 4A. and the extraction direction is a direction from bottom to top (an arrow shown on the left side) on the paper of FIG. 4B. The arrows in the center of FIGS. 4A and 4B indicate directions in which the O-ring 5 moves while changing the sealing position. The movement of the O-ring 5 while changing the sealing position is not limited to movement while rotating, and includes movement while twisting in the insertion/extraction direction or movement similar to the movement while twisting.

The connection structure 1 also includes a cap 4 that is arranged on the coupling 30 and serves as a first stopper for defining a position of the O-ring 5 to prevent the O-ring 5 from coming off. That is, the connection structure 1 generally includes the chamber 2, the connection part 3, the cap 4, and the O-ring 5.

Configuration of the Chamber 2

As shown in FIGS. 2A and 3A, the housing 20 of the chamber 2 is composed of a first housing 21 and a second housing 22. The output port 27 is integrally formed with the first housing 21. A connection port 221 and a connection port 222 are integrally formed on a dome-shaped upper surface 220 of the second housing 22.

The housing 20 is made using a material that is excellent in injection moldability, has good machinability, and additionally is easy to adjust surface roughness. The housing 20 is made using, e.g., a material that can also be welded by ultrasonic welding. Furthermore, the housing 20 is made using a material that is non-toxic to living organisms and has high insulating properties since it may come into contact with human body fluids. Thus, the housing 20 is made using, e.g., polycarbonate. The chamber 2 is thrown away after a single use without being reused since blood flows into the first space 23.

A flow route 211 is formed on a bottom surface 210 inside the first housing 21. In addition, a filter 26 is arranged on the bottom surface 210 so as to cover the flow route 211. The filter 26 is provided so that blood, etc., flowing into the second space 24 does not flow into the flow route 211. The flow route 211 is a path through which the gas K in the second space 24 flows out.

The first housing 21 also has a cylindrical insertion part 28 having a bottom surface 280 (a first bottom surface), and the output port 27 is provided so as to protrude from the bottom surface 280. The output port 27 has a circular cylindrical shape as an example of the cylindrical shape, and has the flow route 211 thereinside. In addition, an end of the output port 27 is tapered and has a tapered surface 271. However, the end of the output port 27 is not limited to the tapered surface, and may have, e.g., an R-shape. In addition, the shape of the output port 27 is not limited to the circular cylindrical shape and may be a square cylinder shape.

The insertion part 28 has a circular cylindrical shape surrounding the output port 27 and is integrally formed with the output port 27. The coupling 30 is inserted into an opening 281 of the insertion part 28.

The first housing 21 further includes, e.g., protrusions 29 protruding from a side surface 282 of the insertion section 28, as shown in FIG. 2A. The protrusions 29 are inserted into, e.g., crank grooves 32 of the connection part 3 shown in FIG. 2B. Two protrusions 29 are formed so as to correspond to the number of the crank grooves 32 of the connection part 3. Alternatively, as a modification, the protrusions 29 may be provided on the connection part 3 and the crank grooves 32 on the first housing 21.

The connection port 221 and the connection port 222 of the second housing 22 are connected to the artery-side blood circuit 11 or the vein-side blood circuit 12. The blood R flowing through the artery-side blood circuit 11 and the vein-side blood circuit 12 flows into, e.g., the first space 23 from the connection port 221, applies the pressure $P_R$ to the diaphragm 25, and flows out from the connection port 222.

The diaphragm 25 has, e.g., a dome shape and is attached to the housing 20 by being sandwiched at an edge thereof between the first housing 21 the second housing 22, as shown in FIG, 3A. The diaphragm 25 is made using a flexible material that can be displaced or deformed with pressure change in the first space 23 and the second space 24. The diaphragm 25 is made using, e.g., a flexible sheet, such as a synthetic rubber sheet made of a silicone rubber, etc., or a vinyl chloride sheet, that can isolate the blood R from the gas K.

Configuration of the Connection Part 3

The connection part 3 has, e.g., a cylindrical guide part 31 having a bottom surface 310 (a second bottom surface), the coupling 30 is provided so as to protrude from the bottom surface 310. and the chamber 2 and the connection part 3 are connected by inserting the insertion part 28 into an opening 311 of the guide part 31, as shown in FIGS. 2B and 3B. The coupling 30 and the guide part 31 are formed as separate members in the first embodiment, but not limited thereto and may be integrally formed.

The connection part 3 is attached to the blood purifying device 9 and is thus not thrown away after a single use, unlike the chamber 2. The connection part 3 is thus made using a material of which rust resistance, stiffness, chemical resistance and weather resistance are high. Thus, the coupling 30 of the connection part 3 is made using, e.g., stainless steel which is a hard material, such as SUS316 or SUS304 so as to have an elongated cylindrical shape, but is not limited thereto and may be non-metal. The guide part 31 is also made using stainless steel such as SUS316 or SUS304 in the same manner as the coupling 30. The coupling 30 in the first embodiment is press-fitted into an insertion hole 315 of the guide part 31. The shape of the coupling 30 is not limited to the circular cylindrical shape and may be a square cylinder shape.

The coupling 30 is provided, e.g., at an end 300 facing a member to be connected thereto (the output port 27), and the cap 4 as a first stopper for defining the position of the O-ring 5 after extracting the member to be connected is attached to the coupling 30 to prevent the O-ring 5 from coming off, as shown in FIG. 3B. In addition, the coupling 30 is provided with a second stopper facing the cap 4 and being separated from the cap 4 by more than a diameter W of the O-ring 5.

In particular, the coupling 30 has, at the end 300 facing the chamber 2, an insertion opening 301 allowing insertion of the O-ring 5 and being connected to a flow route 305 of the gas K. The cap 4 as the first stopper is attached at an end side of the insertion opening 301, and a bottom surface 303 of the insertion opening 301 serves as the second stopper. The insertion opening 301 has a circular shape in a cross section orthogonal to the insertion direction of the output port 27, has an end region 304 having a radius decreasing near the flow route 305, and is configured that the end region 304 is joined to the flow route 305. An end 272 of the output port 27 is inserted into the end region 304. Meanwhile, a terminal end 309 of the coupling 30 is connected to the tube 10b connected to the pressure sensor 1a of the pressure detection unit 10.

At an upper part of the end 300 of the coupling 30. a tapered surface 306 is formed on the outer side and a fitting part 307 is formed on the inner side. The tapered surface 306 is formed to create a space between the coupling 30 and the cap 4. It is possible to easily remove the cap 4 from the coupling 30 by insetting a. tool into the space, with the principle of leverage using the guide part 31 as a fulcrum.

The fitting part 307 is composed of a recessed part 307a recessed from a side surface 302 of the insertion opening 301, and a protruding part 307b as an upper part having a diameter larger than the side surface 302 and protruding with respect to the recessed part 307a, where the recessed part 307a and the protruding part 307b are connected so as to form a smooth S-shaped curve. The fitting part 307 is formed all around the circumferential direction of the insertion opening 301.

The guide part 31 has a tapered surface 313 provided on the opening 311-side of an upper surface 312. The upper surface 312 of the guide part 31 is located higher than the cap 4, as shown in FIG. 3B. Therefore, a trouble such as removal of the cap 4 from the coupling 30 due to accidental contact of a cloth, etc., is less likely to occur during cleaning, etc.

The guide part 31 also has the crank grooves 32 for guiding insertion of the insertion part 28 of the chamber 2 and maintaining a state in which the chamber 2 is inserted and the coupling 30 and the output port 27 are connected via the O-ring 5.

The crank groove 32 includes a vertical groove 320 formed along a direction of insertion of the chamber 2, and a horizontal groove 321 formed in a direction orthogonal to the vertical groove 320, as shown in FIGS. 2A and 2B. The crank grooves 32 are provided so as to face each other across the coupling 30.

When the protrusions 29 of the chamber 2 are fitted into the horizontal grooves 321 by rotating the chamber 2 in a left direction on the paper of FIG. 2B after the protrusions 29 of the chamber 2 are inserted into the vertical grooves 320 and the output port 27 is connected to the coupling 30, the connection between the chamber 2 and the connection part 3 is locked. A protruding claw 311b is formed on a side surface 311a of the opening 311 of the guide part 31 and locks rotation of the chamber 2 relative to the connection part 3 by climbing and passing over a raised part provided on the first housing 21 of the chamber

Configuration of the Cap 4

The cap 4 is made using, e.g., a material of which elasticity, toughness, chemical resistance and weather resistance are high. The cap 4 in the first embodiment is made using, e.g., polypropylene.

The cap 4 includes, e.g., an upper part 40 and a lower part 41, as shown in FIGS. 4A and 4B. The upper part 40 has a disk shape. The upper part 40 has a rounded upper corner formed on an insertion opening 45-side.

A level difference 46 from the upper part 40 is formed on the insertion opening 45-side of the lower part 41. An inclined surface 47 is also formed on the lower part 41 at an end in contact with the O-ring 5. A fitting part 48 fitted to the fitting part 307 of the coupling 30 is also formed on the lower part 41.

The fitting part 48 is composed of a protruding part 48a having a curved surface at a corner corresponding to the recessed part 307a, recessed in an S-shaped, of the fitting part 307, and a recessed part 48b having a shape fitted to the protruding part 307b of the fitting part 307. As shown in FIGS. 4A and 4B, the protruding part 48a of the fitting part 48 does not fit to the recessed part 307a of the fitting part 307 and a gap is formed. This gap is provided to allow the cap 4 to deflects when removing the cap 4 using the principle of leverage described above.

The O-ring 5 has an outer diameter larger than a width of the insertion opening 301 of the coupling 30, as described later. Therefore, the O-ring 5 inserted into the insertion opening 301 is less likely to move down under its own weight. When the inserted chamber 2 is extracted from the connection part 3, the O-ring 5 moves upward while changing the sealing position as the output port 27 moves upward as indicated by the arrow in FIG. 4B. Due to this movement, the O-ring 5 comes into contact with the inclined surface 47 of the cap 4 and applies a force F mainly in a direction perpendicular to the inclined surface 47, i.e., in a direction opposite to a normal direction of the inclined surface 47. The force F is a force pressing the cap 4 against the fitting part 307 and is a force in a direction in which the fitting part 48 of the cap 4 is strongly fitted to the fitting part 307, Therefore, the connection structure 1 has a structure in which the O-ring 5 is less likely to come off from the coupling 30.

After the chamber 2 is extracted from the connection part 3, the O-ring 5 is located at an upper part of the insertion opening 301 as shown in FIG. 4A. Then, when the chamber 2 is inserted into the connection part 3, the O-ring 5 moves downward while changing the sealing position as the output port 27 moves downward as indicated by the arrow in FIG. 4A, and the movement is stopped at the bottom surface 303.

Configuration of the O-ring 5

FIG. 5A is a diagram for explaining an example of a squashing rate of the O-ring in the first embodiment, FIG. 5B is an explanatory diagram illustrating an example of a region damaged when the O-ring does not rotate, and FIG. 5C is an explanatory diagram illustrating an example of a region damaged when the O-ring rotates.

The O-ring 5 is made using a material with high wear resistance, chemical resistance, elasticity (low compression set) and weather resistance and is formed into a ring shape. The O-ring 5 is preferably made of a material further having a low friction, i.e., a small friction coefficient μ, i.e., a low frictional resistance. The O-ring 5 in the first embodiment is formed into a ring shape using a fluoro-rubber that has a rubber hardness of 50°-80° and allows the O-ring 5 to uniformly rotate in a twisting direction. However, the material of the O-ring 5 is not limited thereto as long as it acts as the seal member, and its frictional resistance may be reduced by applying a coating to the surface.

When using the width Di of the output port 27 of the chamber 2, a diameter $D_2$ of the insertion opening 301 of the coupling 30 and the diameter W of the O-ring 5, the relation is expressed by the following expression (1).

$$0<1-(D_1-D_2)/2<W\alpha \quad (1).$$

When the expression (1) is satisfied, the O-ring 5 moves with insertion/extraction while changing the sealing position and also while maintaining the sealing properties. A threshold a is a value that is different depending on the material, size and surface condition of the output port 27, the coupling 30 and the O-ring 5, Although a typical squashed amount is about 8-25% (0.08-0.25 for "$1-(D_1-D_2/2W$"), the squashed amount in the first embodiment is, e.g., ten and several percent.

In case that an attachment groove 30b for attaching the O-ring 5 is formed on a fixing wall 30a and the O-ring is in contact with a first stopper 30c (an upper surface) and a second stopper 30d (a lower surface) of the attachment groove 30b and is thereby restrained from moving while changing the sealing position, and when a sliding member 27a moves downward while being in contact with the O-ring 5 as shown in FIG. 5B, a region 55 rubbing against the sliding member 27a is greatly damaged since the O-ring 5 cannot move while changing the sealing position.

On the other hand, in case that the O-ring comes into contact with the first stopper 30c (the upper surface) and the second stopper 30d (the lower surface) of the attachment groove 30b but is not restrained from moving while changing the sealing position, and when the sliding member 27a moves downward while being in contact with the O-ring 5 as shown in FIG. 5C, the region 55 to be damaged is dispersed and located on the attachment groove 30b-side and the sliding member 27a-side since the O-ring 5 moves downward while changing the sealing position. That is, the region 55 shown in FIG. 5C is wider than the region 55 shown in FIG. 5B. Therefore, surface roughness due to insertion and extraction is less likely to occur on the O-ring 5, i.e., damage on a sealing surface 51 (the surface of the O-ring 5) is suppressed and small, resulting in high insertion/extraction durability and long life.

As shown in FIG. 5A, a movable distance L of the O-ring 5 is set according to a stroke of the output port 27 from when coming into contact with the O-ring 5 to when connection is completed, and is greater than the diameter W of the O-ring 5. The distance L is a distance from an upper part of the inclined surface 47 of the cap 4 to the bottom surface 303.

The chamber 2 is thrown away after a single use, as described above. However, the connection part 3 is attached to the main body 90 of the blood purifying device 9 and is thus not thrown away after a single use. The O-ring 5 is preferably repeatedly usable rather than disposable from a cost perspective and is thus arranged in the connection part 3, but it deteriorates when the insertion and extraction are repeated many times, causing pressure leakage and thus a decrease in detection accuracy, The connection structure 1 in the first embodiment has a long life until a decrease in detection accuracy occurs since it is configured that the O-ring 5 moves while changing the sealing position.

Attachment of the Chamber 2 to the Connection Part 3

FIGS. 6A to 6D) are diagrams illustrating an example of connection between the chamber and the connection part in the connection structure of the first embodiment. FIGS. 7A to 7C are cross sectional views showing the example of connection between the chamber and the connection part in the connection structure of the first embodiment. The connection part 3 will be described as being fixed to the main body 90 of the blood purifying device 9.

As shown in FIGS. 6A and 7A, an end of the insertion part 28 of the chamber 2 is inserted into the opening 311 of the connection part 3, and the protrusions 29 of the chamber 2 are aligned with the vertical grooves 320 of the connection part 3. At this time, the insertion part 28 of the chamber 2 is inserted into the opening 311 while being guided by the guide part 31.

Next, as shown in FIGS. 6B and 7B, when the chamber 2 is further pushed into the connection part 3, the O-ring 5 comes into contact with the tapered surface 271 of the output port 27. In the connection structure 1, it is possible to suppress tilt of the chamber 2 and to vertically insert the output port 27 into the O-ring 5 by configuring that a distance from where the guide by the guide part 31 is started to where the output port 27 comes into contact with the O-ring 5 is long, i.e., a distance that the insertion part 28 moves while being guided by the opening 311 is sufficiently long. When this distance is short, the output port 27 may be inserted into the O-ring 5 in a tilted state. As shown in FIG. 7A, at the time of starting to guide the insertion part 28 by the guide part 31, a distance $L_2$ from the guide start point to a highest point of the O-ring 5 is longer than a distance $L_1$ from the end of the output port 27 to a lower surface 283 of the insertion part 28.

Next, as shown in FIGS. 6C and 7C, when the chamber 2 is further pushed into the connection part 3, a lower surface 283 of the chamber 2 comes into contact with the bottom surface 310 of the connection part 3 and insertion is completed. At this time, since the output port 27 moves while pushing down the O-ring 5, the O-ring 5 moves downward while changing the sealing position. The O-ring 5 then comes into contact with the bottom surface 303 of the coupling 30. At this time, it is possible to move the protrusions 29 of the chamber 2 into the horizontal grooves 321.

Next, as shown in FIG. 6D, the protrusions 29 are moved into the horizontal grooves 321 by rotating the chamber 2, thereby locking the chamber 2 to the connection part 3. When extracting the chamber 2, the above procedure is reversed. The O-ring 5 moves upward with the movement of the output port 27 while changing the sealing position, and then stays at a position in contact with the cap 4.

Figure 8:
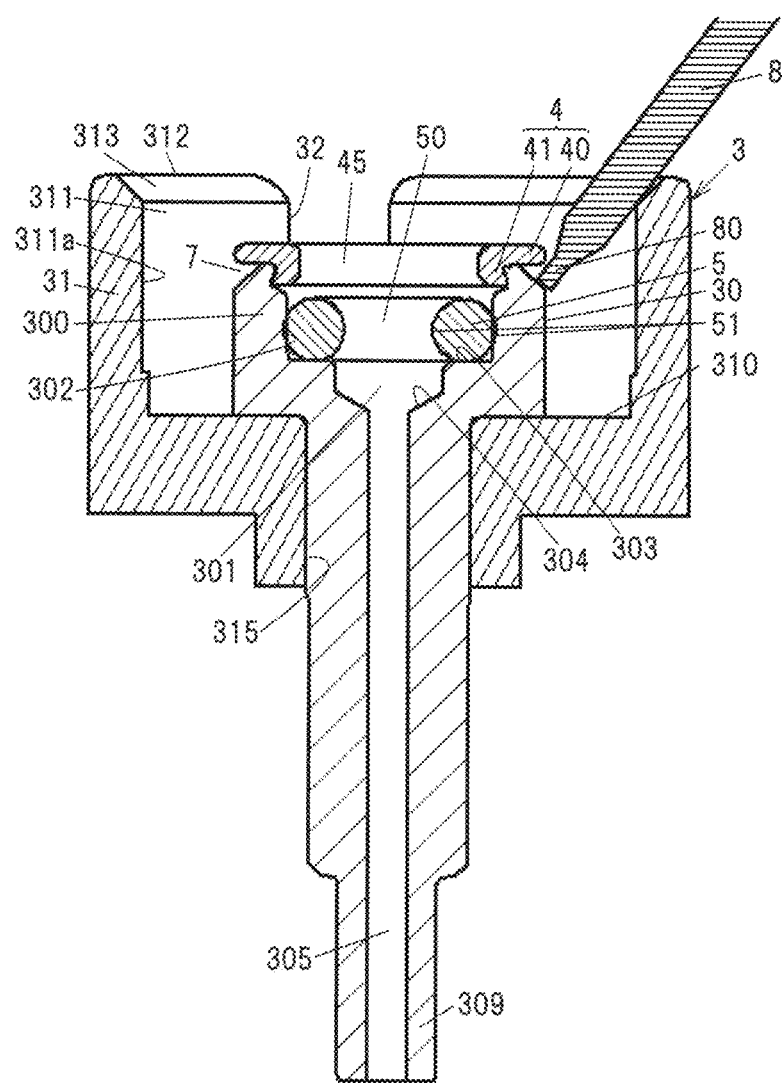
FIG. 8 is an explanatory diagram illustrating an example of replacement of the O-ring in the first embodiment.

FIG. 8 is a diagram for explaining an example of replacement of the O-ring in the first embodiment. As shown in FIG. 8, it is possible to easily remove the cap 4 by inserting a tip 80 of a tool 8 into a gap 7 formed between the cap 4 and the coupling 30, with the principle of leverage using the guide part 31 as a fulcrum. The O-ring 5 after removing the cap 4 is simply fitted into the insertion opening 301 and thus can be easily taken out.

Effects of the First Embodiment

The connection structure 1 in the first embodiment can enhance durability of the O-ring ring 5 that is the seal member. In particular, the connection structure 1 is configured that when the chamber 2 is inserted into/extracted from the connection part 3, the output port 27 comes into contact with the O-ring 5 and the O-ring 5 moves while changing the sealing position. Therefore, as compared to when the seal member does not move while changing the sealing position, damage on the O-ring 5 due to insertion/extraction of the chamber 2 is small and the O-ring 5 has high insertion/extraction durability. Since the O-ring 5 of the connection structure 1 has high insertion/extraction durability and thus has a long replacement cycle, it is possible to reduce the operational cost. Furthermore, since the O-ring 5 has high insertion/extraction durability, the connection structure 1 has a good sealing property and accuracy of pressure detection by the pressure sensor 10a is stabilized.

Since the cap 4 which can be easily removed from the coupling 30 serves as a stopper for the O-ring 5 in the connection structure 1, it is easy to replace the O-ring 5 as compared to when such a configuration is not adopted.

Since the connection structure 1 is configured that the cap 4 is located lower than the upper surface 312 of the guide part 31, it is possible to suppress removal of the cap 4 due to accidental contact of a cloth, etc., during cleaning, as compared to when the cap 4 is located at the same height or higher than the upper surface 312. In addition, since the connection structure 1 is configured that the upper surface 312 of the guide part 31 is located higher than the cap 4 and a tool (a flat-blade screwdriver, etc.) can be easily inserted into the gap 7 between the cap 4 and the coupling 30, it is possible to easily remove the cap 4 with the principle of leverage using the guide part 31 as a fulcrum.

In the connection structure 1, the insertion part 28 is guided by the guide part 31 before the output port 27 comes into contact with the O-ring 5 and tilt of the chamber 2 is thereby suppressed. Therefore, as compared to when such a configuration is not adopted, the output port 27 is vertically inserted into an insertion opening 50 of the O-ring 5. In addition, in the connection structure 1, since such vertical insertion allows the O-ring 5 to uniformly rotate in the twisting direction, the O-ring is less likely to be subjected to a local load and thus can maintain sealing performance for a long time.

Since the connection structure 1 is adopted in the blood purifying device 9, the O-ring 5 has a long replacement cycle of the O-ring 5 and detection accuracy of pressure of the blood R can be maintained for a long time. Therefore, the operational cost is suppressed and performance can be maintained for a long time.

Second Embodiment

The second embodiment is different from other embodiments in that the connection structure 1 is composed of the chamber 2, the connection part 3, and the O-ring 5.

Figure 9A:
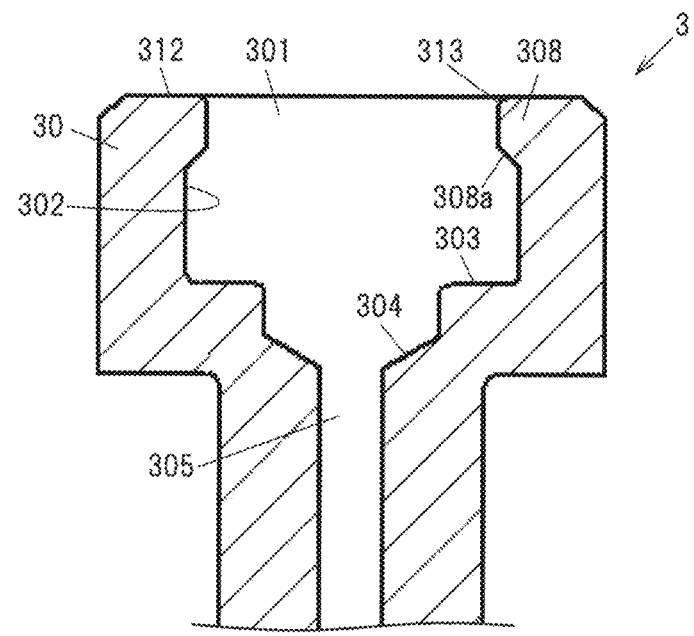
FIG. 9A is a cross sectional view showing an example of a coupling in the second embodiment.

FIG. 9A is a cross sectional view showing an example of the coupling in the second embodiment. In the embodiment described below, portions having the same functions and configurations as those in the first embodiment are denoted by the same reference numerals as those in the first embodiment, and the explanation thereof will omitted.

The coupling 30 in the second embodiment includes a first stopper 308 that is provided at the end 300 facing the chamber 2 and defines the position of the O-ring 5 after extracting the output port 27 to prevent the O-ring 5 from coming off, as shown in FIG. 9A.

The first stopper 308 protrudes beyond the side surface 302 of the insertion opening 301, i.e., a distance is shorter than a distance between the side surfaces 302. The first stopper 308 has a tapered surface 308a formed on a lower side. Before the output port 27 of the chamber 2 is inserted, the O-ring 5 is in contact with the tapered surface 308a.

Since the connection structure 1 in the second embodiment does not use the cap, the number of parts is reduced and the cost is thus reduced.

Third Embodiment

The third embodiment is different from the other embodiments in that the side surface 302 of the coupling 30 in the connection structure 1 of the second embodiment is configured to have a tapered shape.

Figure 9B:
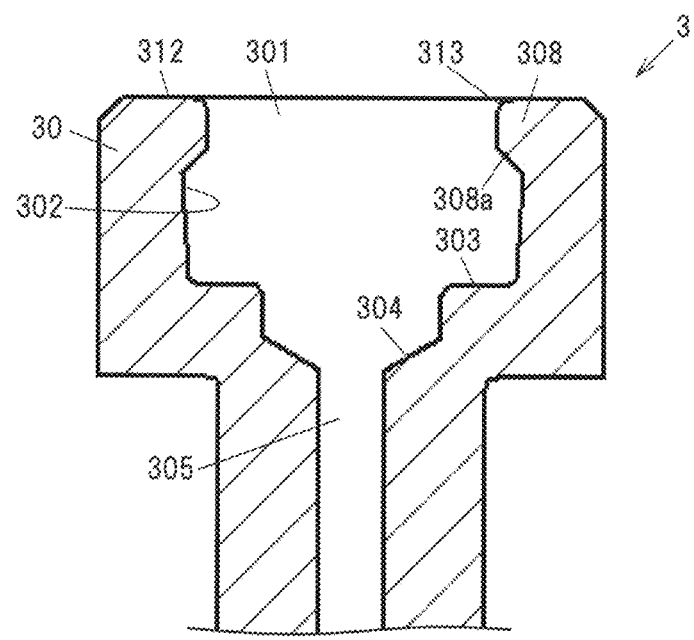
FIG. 9B is a cross sectional view showing the example of a coupling in the third embodiment.

FIG. 9B is a cross sectional view showing an example of the coupling in the third embodiment. In the third embodiment, the side surface 302 of the coupling 30 has a tapered shape, as shown in FIG. 9B. The side surface 302 is formed so that the upper side on the paper of FIG. 9B is a wide and the lower side is narrow. Thus, the O-ring 5 before insertion of the output port 27 easily stays at an upper part of the insertion opening 301, i.e., at a position in contact with the first stopper 308.

In the connection structure 1 of the third embodiment, the position of the O-ring 5 before connecting the chamber 2 to the connection part 3 is stable. Therefore, as compared to when the insertion opening 301 does not have a tapered shape, the output port 27 of the chamber 2 easily comes into contact with the O-ring 5 at a designed position. In addition, since the connection structure 1 has the insertion opening 301 of which diameter changes continuously, it is easy to design the shape of the O-ring 5 as compared to when the tapered shape is not formed.

Fourth Embodiment

The fourth embodiment is different from other embodiments in that the O-ring 5 is arranged on the chamber 2 side.

FIGS. 10E to 10C are diagrams illustrating an example of the connection structure in the fourth embodiment. FIG. 10A shows the state at the start of insertion of the chamber 2 into the connection part 3. FIG. 10B shows the state during the insertion. FIG. 10C shows the state at the end of the insertion.

As shown in FIGS. 10A to 10C, the output port 27 of the connection structure 1 in the fourth embodiment includes a first stopper 273 that is provided at an end facing the coupling 30 and defines the position of the O-ring 5 to prevent the O-ring 5 from coming off, and a second stopper 274 that is provided so as to face the first stopper 273 and separated from the first stopper 273 by more than the diameter of the O-ring 5. In this connection structure 1, by connection of the chamber 2 to the connection part 3, the O-ring 5 moves from the first stopper 273-side to the second stopper 274-side of the output port 27 while changing the sealing position.

Fifth Embodiment

The fifth embodiment is different from the other embodiments in that the side surface 302 of the coupling 30 in the connection structure 1 of the fourth embodiment is configured to have a tapered shape.

FIGS. 11A to 11C are diagrams illustrating an example of the connection structure in the fifth embodiment. FIG. 11A shows the state at the start of insertion of the chamber 2 into the connection part 3. FIG. 11B shows the state during the insertion. FIG. 11C shows the state at the end of the insertion.

The connection structure 1 in the fifth embodiment is configured that the side surface 302 of the coupling 30 has a tapered shape, as shown in FIGS. 11A to 11C.

In this connection structure 1, by connection of the chamber 2 to the connection part 3, the O-ring 5 moves from the first stopper 273-side to the second stopper 274-side of the output port 27 while rotating. At this time, the O-ring 5 moves with a varying squashing rate while changing the sealing position since the distance between the side surface 270 of the output port 27 and the side surface 302 of the coupling 30 decreases toward the lower side on the paper of FIGS. 11A, to 11C. The variation in the squashing rate is variation in a squashing rate-decreasing direction.

Sixth Embodiment

The sixth embodiment is different from the other embodiments in that the side surface 270 of the coupling 27 has an inverted tapered shape.

FIGS. 12A to 12C are diagrams illustrating an example of the connection structure in the sixth embodiment. FIG. 12A shows the state at the start of insertion of the chamber 2 into the connection part 3. FIG. 12B shows the state during the insertion. FIG. 12C shows the state at the end of the insertion.

The connection structure 1 in the sixth embodiment is configured that the side surface 270 of the output port 27 has a tapered shape, as shown in FIGS. 12A to 12C. The distance between the side surface 270 of the output port 27 and the side surface 302 of the coupling 30 is long on the lower side on the paper of FIGS. 124 to 12C and short on the upper side, unlike the other embodiments. That is, the tapered shape of the side surface 270 in the sixth embodiment is tapered in a direction opposite to the tapered shape in the other embodiments, i.e., an inverted tapered shape.

In this connection structure 1, by connection of the chamber 2 to the connection part 3, the O-ring 5 moves from the first stopper 273-side to the second stopper 274-side of the output port 27 while changing the sealing position. However, the O-ring 5 moves with a squashing rate varying in a squashing rate-increasing direction while changing the sealing position since the distance between the side surface 270 of the output port 27 and the side surface 302 of the coupling 30 increases toward the lower side on the paper of FIGS. 12A to 12C.

Seventh Embodiment

The seventh embodiment is different from the other embodiments in that both the side surface 270 of the coupling 27 and the side surface 302 of the coupling 30 have a tapered shape.

Figure 13A:
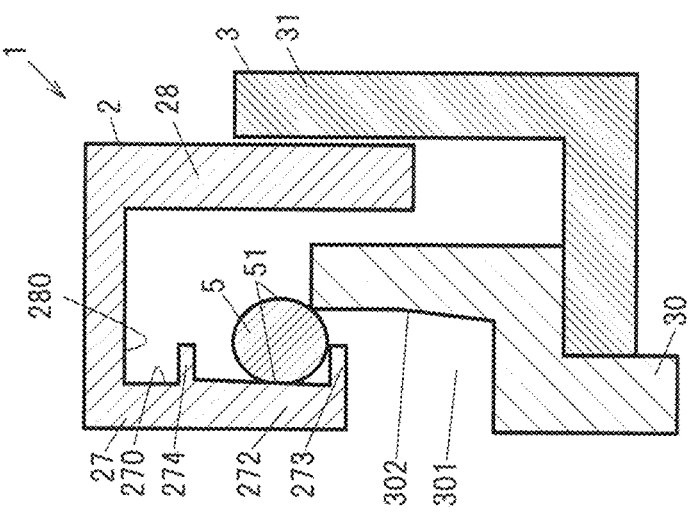
FIG. 13A is a diagram illustrating an example at the start of insertion of the chamber into the connection part in the connection structure of the seventh embodiment.
Figure 13B:
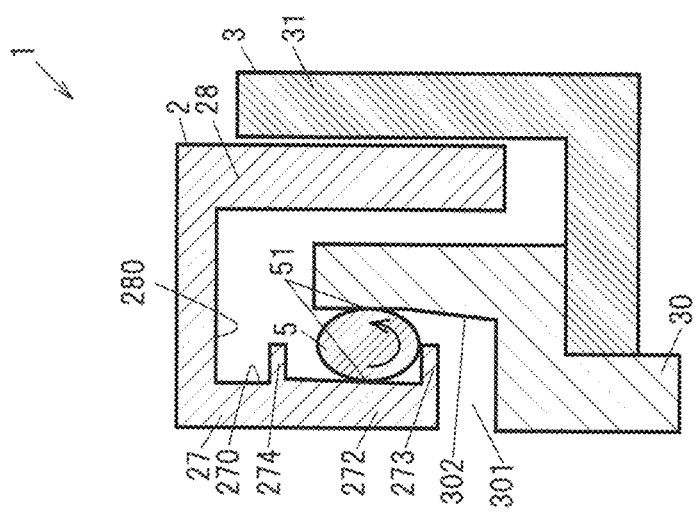
FIG. 13B is a diagram illustrating an example during insertion of the chamber into the connection part in the connection structure of the seventh embodiment.
Figure 13C:
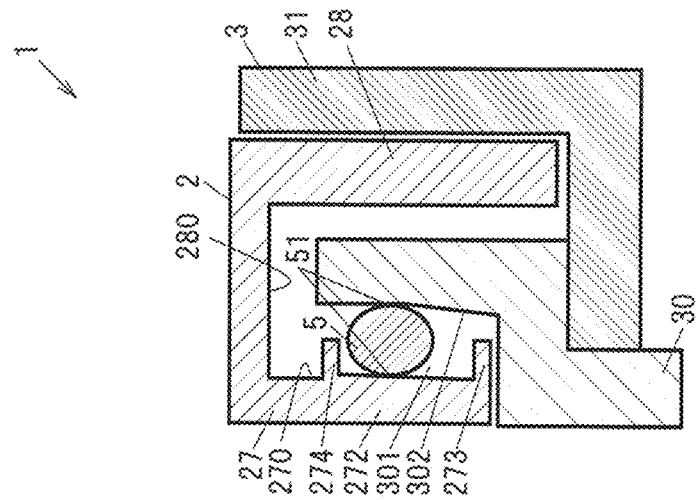
FIG. 13C is a diagram illustrating an example at the end of insertion of the chamber into the connection part in the connection structure of the seventh embodiment.

FIGS. 13A to 13C are diagrams illustrating an example of the connection structure in the seventh embodiment. FIG. 13A shows the state at the start of insertion of the chamber 2 into the connection part 3. FIG. 13B shows the state during the insertion. FIG. 13C shows the state at the end of the insertion.

The connection structure 1 in the seventh embodiment is configured that the side surface 270 of the output port 27 and the side surface 302 of the coupling 30 have a tapered shape, as shown in FIGS. 13A to 13C. The side surface 302 of the coupling 30 is vertical on the upper side on the paper of FIGS. 13A to 13C and has a tapered shape on the lower. This tapered shape is a shape in which the lower side is thicker.

In this connection structure 1, by connection of the chamber 2 to the connection part 3, the O-ring 5 moves from the first stopper 273-side to the second stopper 274-side of the output port 27 while changing the sealing position. At this time, the O-ring 5 moves with a varying squashing rate, but the squashing rate can be made constant from middle by adjusting the tapered shapes of the output port 27 and the coupling 30.

Eighth Embodiment

Figure 14:
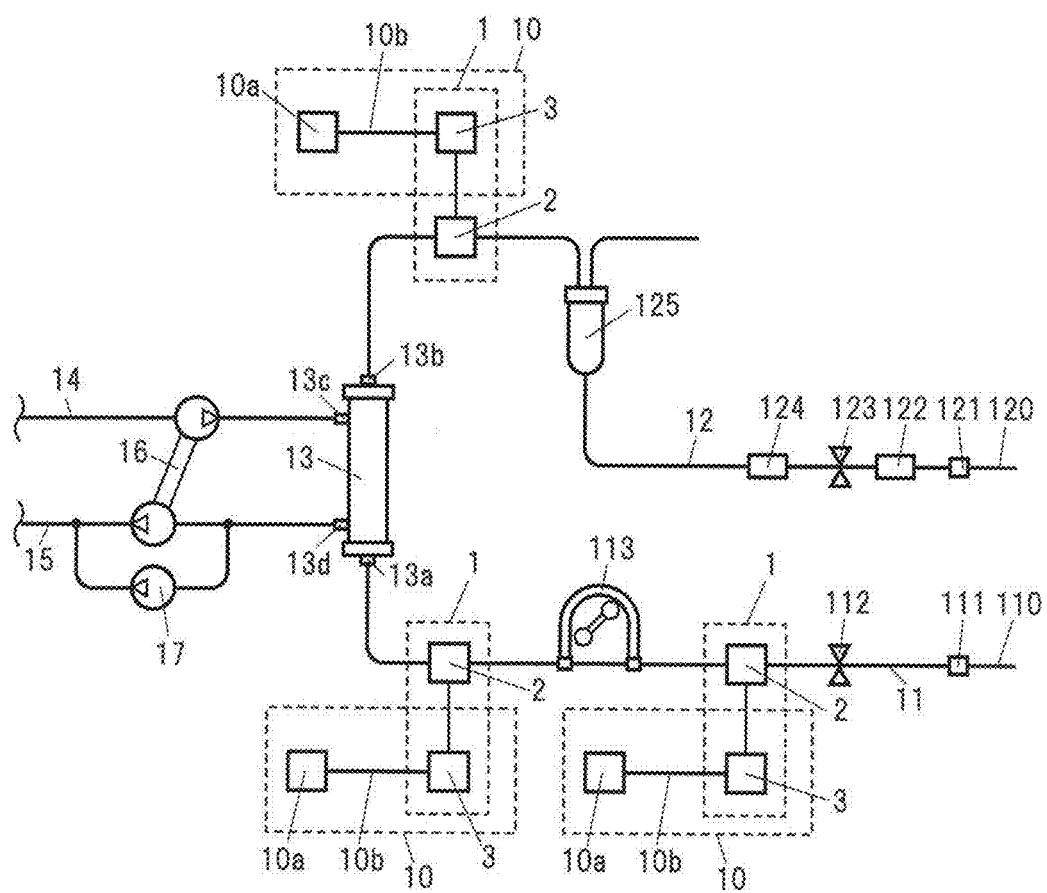
FIG. 14 is a diagram illustrating an example configuration of the blood purifying device in the eighth embodiment.

The eighth embodiment is different from other embodiments in that the pressure detection units 10 are arranged before and after the blood pump 113, as shown in FIG. 14.

FIG. 14 is a diagram illustrating an example configuration of the blood purifying device in the eighth embodiment. In the eighth embodiment, an additional pressure detection unit 10 is arranged between the clamp 112 of the artery-side blood circuit 11 and the blood pump 113, i.e., the pressure detection units 10 are arranged before and after the blood pump 113.

Therefore, the blood purifying device 9 can detect pressure of blood before and after the blood pump 113 and thus can control the blood pump 113 more appropriately as compared to when providing either before or after, hence, accuracy of blood pressure management is improved. In addition, even when the number of the pressure detection units 10 is increased, the service life of the O-ring 5 is prolonged by adopting the connection structure 1. Therefore, the operational cost of the blood purifying device 9 can be reduced as compared to when the connection structure 1 is not adopted.

Ninth Embodiment

The ninth embodiment is different from other embodiments in that the cap 4 is screwed onto and connected to the coupling 30.

Figure 15C:
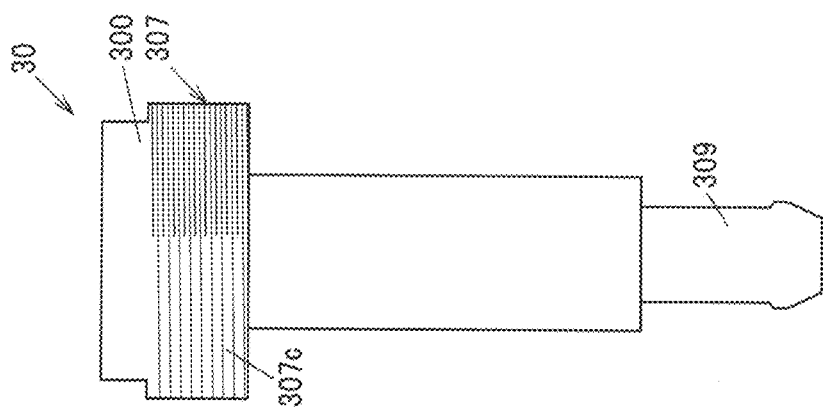
FIG. 15C is a side view showing an example of the coupling in the ninth embodiment.
Figure 15B:
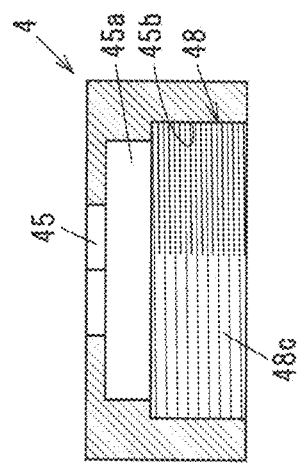
FIG. 15B is a cross sectional view showing an example of a cap in the ninth embodiment.
Figure 16B:
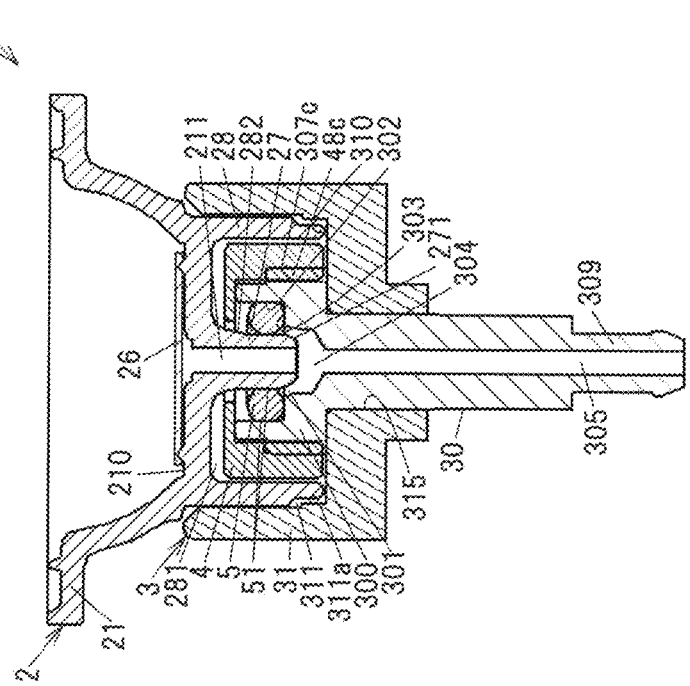
FIG. 16B is a cross sectional view showing an example of when the chamber is connected to the connection part in the ninth embodiment.
Figure 16A:
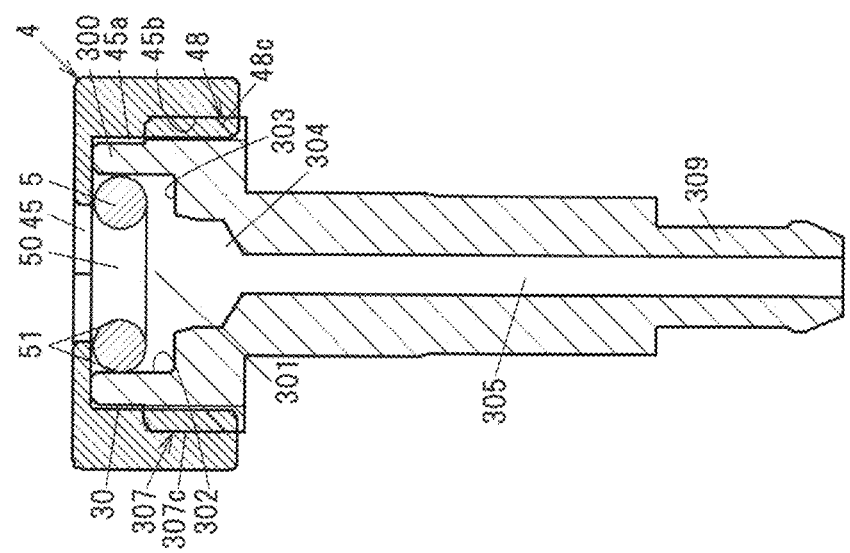
FIG. 16A is a cross sectional view showing an example of the coupling with the cap attached thereto in the ninth embodiment.

FIG. 154 is a perspective view showing an example of the connection structure in the ninth embodiment, FIG. 15B is a cross sectional view showing an example of the cap, and FIG. 15C is a side view showing an example of the coupling. FIG. 16A is a cross sectional view showing an example of the coupling with the cap attached thereto in the ninth embodiment, and FIG. 16B is a cross sectional view showing an example of when the chamber is connected to the connection part. In FIG. 16B, only the first housing 21 of the chamber 2 is shown.

In the connection structure 1 of the ninth embodiment, the cap 4 is screwed onto and connected to the coupling 30, e.g., as shown in FIGS. 15A to 16B.

The cap 4 is made using a resin material or a metal material and is formed into a circular cylindrical shape. The cap 4 also has an internal space 45a connected to the insertion opening 45 into which the output port 27 is inserted, as shown in FIG. 15B. The fitting part 48 is provided on an inner wall 45b of the internal space 45a. The fitting part 48 in the ninth embodiment is configured as a female thread part 48c.

Figure 15A:
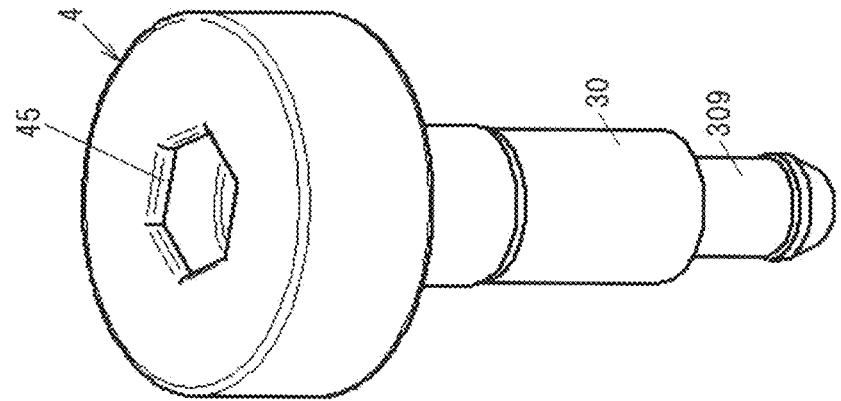
FIG. 15A is a perspective view showing an example of the connection structure in the ninth embodiment.

The insertion opening 45 in the ninth embodiment has a hexagonal shape, as shown in FIG. 15A. Therefore, the cap 4 is screwed onto and connected to the coupling 30 by inserting a hexagonal wrench corresponding to the insertion opening 45 and rotating it relative to the coupling 30.

The shape of the insertion opening 45 is not limited to the hexagonal shape and may be a shape which allows insertion of the output port 27 of the chamber 2 and also corresponds to the shape of a tool to be used, such as a hex robe. Optionally, the outer shape of the cap 4 may be a hexagonal shape, etc., onto which a tool such as a socket wrench can be fitted.

The fitting part 307 is provided on the end 300 located on the upper side of the coupling 30, as shown in FIG. 15C. The fitting part 307 in the ninth embodiment is configured as a male screw part 307c. After the O-ring 5 is arranged in the insertion opening 301 of the coupling 30, the female screw part 48c of the cap 4 is inserted into the male screw part 307c. Then, by rotating the cap 4 relative to the coupling 30, the female screw part 48c is screw-connected to the male screw part 307c and the cap 4 is connected to the coupling 30.

In the connection structure 1 in the ninth embodiment, since the fitting part 48 of the cap 4 is screwed onto and connected to the fitting part 307 of the connection part 3, it is easy to remove the cap 4 as compared to when such a configuration is not adopted, in addition, since the connection structure 1 is configured in that the cap 4 can be removed by inserting a tool into the insertion opening 45 of the cap 4, the cap 4 can be removed more easily and damage on the guide part 31, etc., by the tool is also suppressed as compared to when such a configuration is not adopted.

In the connection structure 1 in at least one of the embodiments described above and the blood purifying device 9 adopting the connection structure 1, it is possible to enhance durability of the seal member.

EXAMPLE

Figure 17A:
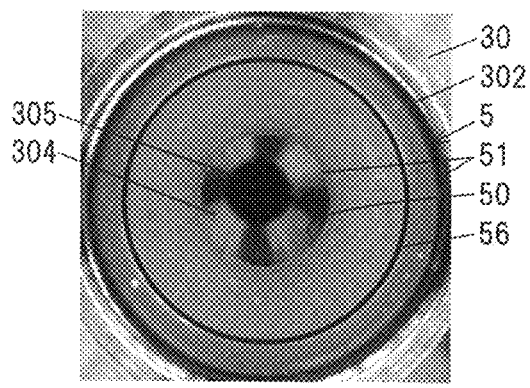
FIG. 17A is a diagram illustrating a surface condition of the O-ring in Example after 500 times of insertion and extraction of the chamber into/from the coupling when a rolling margin is 0.8 mm.
Figure 17B:
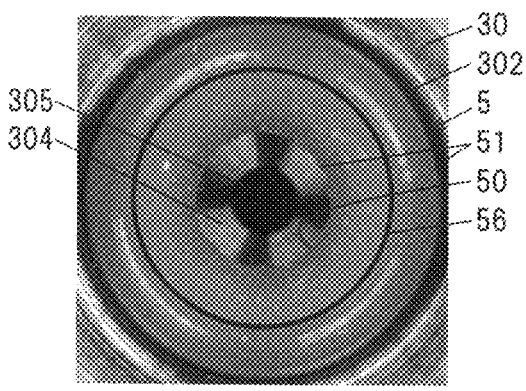
FIG. 17B is a diagram illustrating the surface condition of the O-ring in Example after 500 times of insertion and extraction of the chamber into/from the coupling when the rolling margin is 0.4 mm.
Figure 17C:
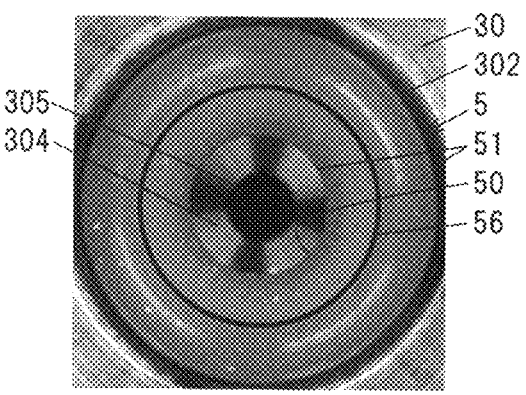
FIG. 17C is a diagram illustrating the surface condition of the O-ring in Example after 500 times of insertion and extraction of the chamber into/from the coupling when the rolling margin is 0 mm.
Figure 18A:
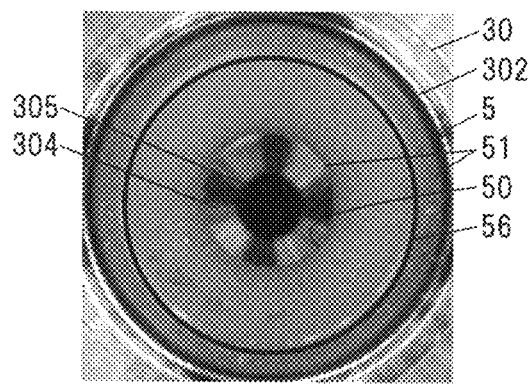
FIG. 18A is a diagram illustrating the surface condition of the O-ring in Example after 1000 times of insertion and extraction of the chamber into/from the coupling when the rolling margin is 0.8 mm.
Figure 18B:
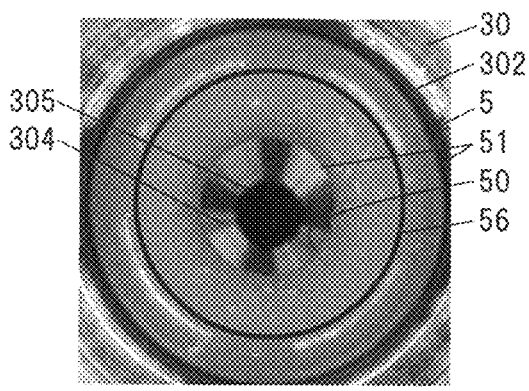
FIG. 18B is a diagram illustrating the surface condition of the O-ring in Example after 1000 times of insertion and extraction of the chamber into/from the coupling when the rolling margin is 0.4 mm.
Figure 18C:
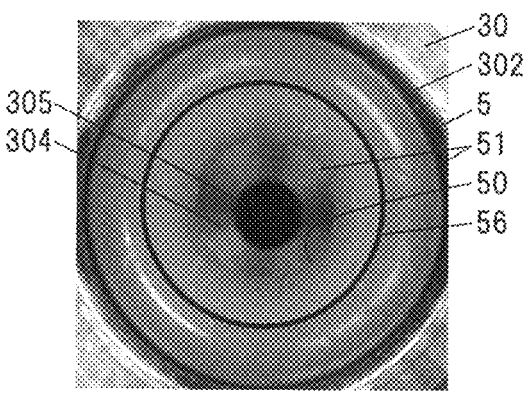
FIG. 18C is a diagram illustrating the surface condition of the O-ring in Example after 1000 times of insertion and extraction of the chamber into/from the coupling when the rolling margin is 0 mm.
Figure 19A:
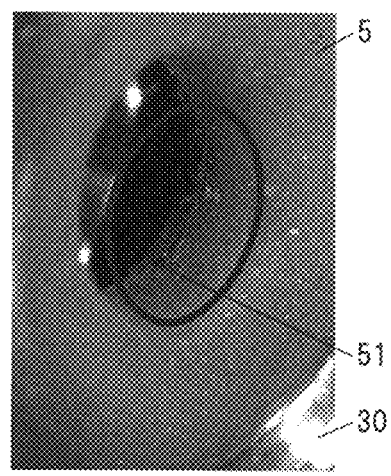
FIG. 19A is an enlarged view showing the surface condition on the inner peripheral side of the O-ring in Example after 1000 times of insertion and extraction of the chamber into/from the coupling when the rolling margin is 0.8 mm.
Figure 19B:
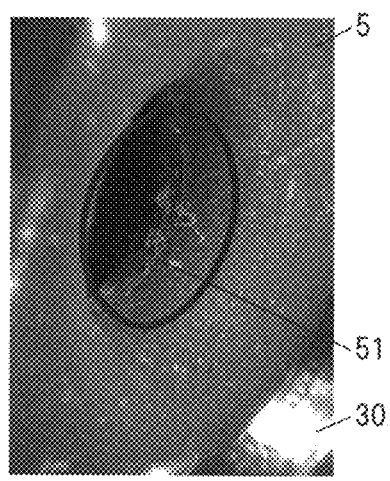
FIG. 19B is an enlarged view showing the surface condition on the inner peripheral side of the O-ring in Example after 1000 times of insertion and extraction of the chamber into/from the coupling when the rolling margin is 0.4 mm.
Figure 19C:
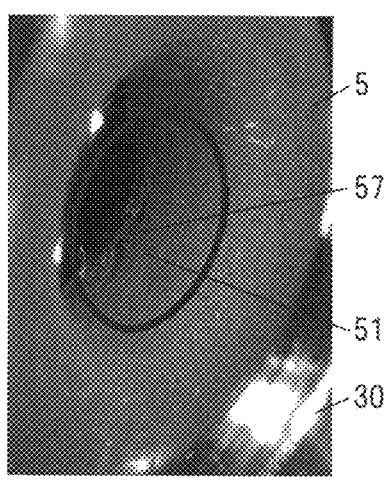
FIG. 19C is an enlarged view showing the surface condition on the inner peripheral side of the O-ring in Example after 1000 times of insertion and extraction of the chamber into/from the coupling when the rolling margin is 0 mm.

FIGS. 17A to 17C are diagrams illustrating a surface condition of the O-ring after 500 times of insertion and extraction of the chamber into/from the coupling. FIGS. 18A to 18C are diagrams illustrating the surface condition of the O-ring after 1000 times of insertion and extraction of the chamber into/from the coupling. FIGS. 19A to 19C are enlarged views showing the surface condition on the inner peripheral side of the O-ring.

In case of FIGS. 17A, 184 and 19A, a rolling margin of the O-ring 5 is 0.8 mm. In case of FIGS. 17B, 18B and 19B, the rolling margin of the O-ring 5 is 0.4 mm. In case of FIGS. 17C, 18C and 19C, the rolling margin of the O-ring 5 is 0 mm. This rolling margin is a movable distance of the O-ring 5, in other words, a play (gap length) for the O-ring 5 inside the insertion opening 301 in the insertion/extraction direction of the chamber 2, and is a distance from the lower part of the O-ring 5 to the bottom surface 303 of the coupling 30 in a state in which the O-ring 5 is in contact with the cap 4, as shown in FIG. 3B. The longer the rolling margin, the easier it is for the O-ring 5 to move while changing the sealing position, Areas encircled by solid lines in FIGS. 174 to 18C show rough regions 56. The rough region 56 means a region in which the encircled surface of the O-ring 5 is roughened by insertion/extraction of the chamber 2.

Furthermore, in FIG. 19A, a hollowed-out spot occurred on the sealing surface 51 on the inner peripheral side after 800 times of insertion/extraction is encircled by a solid line. In FIG. 19B, a hollowed-out spot occurred on the sealing surface 51 on the inner peripheral side after 500 times of insertion/extraction is encircled by a solid line. In FIG. 19C, a hollowed-out spot occurred on the sealing surface 51 on the inner peripheral side after 200 times of insertion/extraction is encircled by a solid line.

The timing at which the hollowed-out spot appears on the sealing surface 51 on the inner peripheral side of the O-ring 5 is in the order of 0 mm, 0.4 mm and 0.8 mm from the earliest, as shown in FIGS. 17A to 19C. In addition, the size of the hollowed-out spot occurred on the sealing surface 51 of the O-ring 5 increases as the rolling margin decreases, as shown in FIGS. 19A to 19C. Particularly, a hollowed-out spot 57 shown in FIG. 19C appeared after 200 times of insertion/extraction but the sealing surface 51 is largely torn despite that the number of times of insertion and extraction is smaller than when the rolling margin is 0.8 mm (the number of times of insertion/removal is 800 times) shown in FIG. 19A and when the rolling margin is 0.4 mm (the number of times of insertion/removal is 500 times) shown in FIG. 19B. The hollowed-out spot here means unacceptable roughness or local rupture causing pressure leakage, and is roughness or rupture causing a problem in use, i.e., roughness and rupture causing a decrease in accuracy of pressure detection by the pressure sensor 10a.

In addition, the size of the rough region 56 of the O-ring S increases in the order of 0.8 mm, 0.4 mm and 0 mm, as shown in FIGS. 17A to 19C. When the rolling margin is larger, it is easier for the O-ring S to move while changing the sealing position and the O-ring 5 is in contact with the inserted chamber 2 in a wider area, hence, the rough region 56 is wider.

From the above, the following relation is established.

When it is easy for the O-ring 5 to move while changing the sealing position, the rough region 56 is wide. In this case, local roughness is less likely to occur on the O-ring 5 which thus has good durability.

When it is difficult for the O-ring 5 to move while changing the sealing position, the rough region 56 is narrow. In this case, local roughness is likely to occur on the O-ring 5 which thus has poor durability.

This means that local roughness on the O-ring 5 decreases with an increase in the rough region 56.

The connection structure 1 is configured such that the O-ring 5 easily moves while changing the sealing position. Therefore, in the connection structure 1 and the blood purifying device 9 adopting the connection structure 1, the rough region 56 of the O-ring 5 is wide and the O-ring 5 has good durability.

Summary of the Embodiments

Technical ideas understood from the plural embodiments described above will be described below citing the reference numerals, etc., used for the embodiments. However, each reference numeral, etc., described below is not intended to limit the constituent elements in the claims to the members, etc., specifically described in the embodiments.

[1] A connection structure (1), comprising: a chamber (2) comprising a hollow housing (20), a diaphragm (25) dividing the inside of the housing (20) into a first space (23) and a second space (24), and an output port (27) outputting a gas (K) in the second space (24) with deformation of the diaphragm (25) caused by pressure (PR) of a fluid (blood R) flowing into the first space (23); a connection part (3) comprising a coupling (30) connected to the output port (27) and being attached to a pressure detection device (main body 90) comprising a pressure sensor (10a) for detecting pressure ($P_K$) of the gas (K) output from the coupling (30); and a seal member (O-ring 5) being sandwiched between a side surface (270) of the output port (27) and a side surface (320) of the coupling (30) and moving while changing a sealing position when connecting or extracting the chamber (2) to/from the connection part (3).

[2] The connection structure (1) described in 111, wherein at least one of the side surface (270) of the output port (27) and the side surface (302) of the coupling (30) has a tapered shape.

[3] The connection structure (1) described in [1] or [2], comprising: a first stopper (273 or 308) being arranged on the side surface (270) of the output port (27) and the side surface (302) of the coupling (30) and defining a position of the seal member (O-ring 5) to prevent the seal member (O-ring 5) from coming off; and a second stopper (274 or bottom surface 303) being arranged on the side surface (270) of the output port (27) or the side surface (302) of the coupling (30) at a position facing the first stopper (273 or 308) and separated from the first stopper (273 or 308) by more than a diameter (W) of the seal member (O-ring 5).

[4] The connection structure (1) described in [3], wherein the coupling (30) comprises, at an end (300) facing the chamber (2), an insertion opening (301) allowing insertion of the seal member (O-ring 5) and being connected to a flow route (211) of the gas (K), the first stopper (308) is provided on an end side of the insertion opening (301), and a bottom surface (303) of the insertion opening (301) serves as the second stopper.

[5] The connection structure (1) described in [4], wherein the first stopper comprises a cap (4) attached to the end (300).

[6] The connection structure (1) described in any one of [1] to [5], wherein the chamber (2) comprises a cylindrical insertion part (28) comprising a first bottom surface (bottom surface 280) and is configured that the output port (27) is provided so as to protrude from the first bottom surface (bottom surface 280), the connection part (3) comprises a cylindrical guide part (31) comprising a second bottom surface (bottom surface 310) and is configured that the coupling (30) is provided so as to protrude from the second bottom surface (bottom surface 310), and the chamber (2) and the connection part (3) are connected by inserting the insertion part (28) into an opening (311) of the guide part (31).

[7] A blood purifying device (9), comprising: the connection structure (1) described in any one of [1] to [6]; a circuit (artery-side blood circuit H and vein-side blood circuit 12) capable of circulating human blood (R) or dialysate; and a blood purifying device-main body (90) to which the liquid circuit (artery-side blood circuit 11 and vein-side blood circuit 12) is attached via the connection structure (1) and which purifies the blood (R) while detecting, as the pressure detection device, pressure ($P_R$) of the blood (R) or dialysate circulating in the circuit (artery-side blood circuit 11 and vein-side blood circuit 12).

The blood purifying device (9) described in [7], wherein the liquid circuit (artery-side blood circuit 11 and vein-side blood circuit 12) is a disposable product to be discarded after each blood purification treatment, the chamber (2) is provided on the liquid circuit (artery-side blood circuit 11 and vein-side blood circuit 12), and the connection part (3) and the seal member (O-ring 5) are provided in the blood purifying device-main body (90).

A blood purifying device (9), comprising: the connection structure (1) described in any one of [1] to [6]; a liquid circuit (artery-side blood circuit 11 and vein-side blood circuit 12) being capable of circulating human blood (R) or dialysate and being a disposable product to be discarded after each blood purification treatment; a blood purifying device-main body (90) to which the liquid circuit (artery-side blood circuit 11 and vein-side blood circuit 12) is attached via the connection structure (1); and a sealing member (cap 4) removably sealing the seal member (O-ring 5) inside the blood purifying device-main body (90), wherein the chamber (2) is provided on the liquid circuit (artery-side blood circuit 11 and vein-side blood circuit 12), and the connection part (3) and the seal member (O-ring 5) are provided In the blood purifying device-main body (90).

Although some embodiments, Example and modifications of the invention have been described, these embodiments. Example and modifications are merely examples and the invention according to claims is not to be limited thereto. These new embodiments, Example and modifications may be implemented in various other forms, and various omissions, substitutions and changes, etc., can be made without departing from the gist of the invention. In addition, all combinations of the features described in these embodiments. Example and modifications are not necessary to solve the problem of the invention. Further, these embodiments. Example and modifications are included within the scope and gist of the invention and also within the invention described in the claims and the range of equivalency.

REFERENCE SIGNS LIST

1: connection structure
2: chamber
3: connection part
4: cap
5: O-ring
9: blood purifying device
10a: pressure sensor
11: artery-side blood circuit
12: vein-side blood circuit
13: dialyzer
13a: blood introduction port
13b: blood discharge port
13c: dialysate introduction port
20: housing
23: first space
24: second space
25: diaphragm
27: output port
28: insertion part
30: coupling 31: guide part
90: main body
211: flow route
270: side surface
273: first stopper
274: second stopper
280: bottom surface
300: end
301: insertion opening
302: side surface
303: bottom surface
308: first stopper
310: bottom surface
311: opening

The invention claimed is:

1. A connection structure, comprising:
a chamber comprising a hollow housing, a diaphragm dividing an inside of the hollow housing into a first space and a second space, and an output port outputting a gas in the second space with deformation of the diaphragm caused by pressure of a fluid flowing into the first space;
a connection part comprising a coupling connected to the output port and being attached to a pressure detection device comprising a pressure sensor for detecting pressure of the gas output from the coupling, wherein the coupling includes a first stopper and a second stopper; and
a seal member being sandwiched between an outer surface of the output port and an inner surface of the coupling and moving while changing a sealing position when connecting or extracting the chamber to/from the connection part, the seal member fits into a space surrounded by the inner surface of the coupling, the first stopper, and the second stopper.

2. The connection structure according to claim 1, wherein at least one of the outer surface of the output port and the inner surface of the coupling has a tapered shape.

3. The connection structure according to claim 1, wherein the first stopper is arranged on the outer surface of the output port or on the inner surface of the coupling and defining a position of the seal member to prevent the seal member from coming off; and
the second stopper is arranged on the outer surface of the output port or on the inner surface of the coupling at a position facing the first stopper and separated from the first stopper by more than a diameter of the seal member.

4. The connection structure according to claim 3, wherein the coupling comprises, at an end facing the chamber, an insertion opening allowing insertion of the seal member and being connected to a flow route of the gas, the first stopper is provided on an end side of the insertion opening, and a bottom surface of the insertion opening serves as the second stopper.

5. The connection structure according to claim 4, wherein the first stopper comprises a cap attached to the end.

6. The connection structure according to claim 1, wherein the chamber comprises a cylindrical insertion part comprising a first bottom surface and is configured that the output port is provided so as to protrude from the first bottom surface, the connection part comprises a cylindrical guide part comprising a second bottom surface and is configured that the coupling is provided so as to protrude from the second bottom surface, and the chamber and the connection part are connected by inserting the cylindrical insertion part into an opening of the cylindrical guide part.

7. A blood purifying device, comprising:
the connection structure according to claim 1;
a liquid circuit capable of circulating human blood or dialysate; and
a blood purifying device-main body to which the liquid circuit is attached via the connection structure and which purifies the blood while detecting, as the pressure detection device, pressure of the blood or dialysate circulating in the liquid circuit.

8. The blood purifying device according to claim 7, wherein the liquid circuit is a disposable product to be discarded after each blood purification treatment, the chamber is provided on the liquid circuit, and the connection part and the seal member are provided in the blood purifying device-main body.

9. A blood purifying device, comprising:
the connection structure according to claim 1;
a liquid circuit being capable of circulating human blood or dialysate and being a disposable product to be discarded after each blood purification treatment;
a blood purifying device-main body to which the liquid circuit is attached via the connection structure; and
a sealing member removably sealing the seal member inside the blood purifying device-main body,
wherein the chamber is provided on the liquid circuit, and the connection part and the seal member are provided in the blood purifying device-main body.

* * * * *